(12) United States Patent
Wu et al.

(10) Patent No.: US 11,116,833 B2
(45) Date of Patent: Sep. 14, 2021

(54) METHOD AND SYSTEM FOR INACTIVATING VIRUS INFECTIVITY FOR PRODUCING LIVE-ATTENUATED VACCINES

(71) Applicant: George Mason University, Fairfax, VA (US)

(72) Inventors: Yuntao Wu, Fairfax, VA (US); Yajing Fu, Fairfax, VA (US); Deemah Dabbagh, Fairfax, VA (US); Zheng Zhou, Fairfax, VA (US)

(73) Assignee: George Mason University, Fairfax, VA (US)

( * ) Notice: Subject to any disclaimer, the term of this patent is extended or adjusted under 35 U.S.C. 154(b) by 0 days.

(21) Appl. No.: 16/271,100

(22) Filed: Feb. 8, 2019

(65) Prior Publication Data

US 2019/0240318 A1    Aug. 8, 2019

Related U.S. Application Data

(60) Provisional application No. 62/628,073, filed on Feb. 8, 2018.

(51) Int. Cl.

| | |
|---|---|
| *A61K 39/21* | (2006.01) |
| *A61P 31/18* | (2006.01) |
| *A61K 39/12* | (2006.01) |
| *C12N 7/00* | (2006.01) |
| *A61K 39/00* | (2006.01) |

(52) U.S. Cl.
CPC .............. *A61K 39/21* (2013.01); *A61K 39/12* (2013.01); *A61P 31/18* (2018.01); *C12N 7/00* (2013.01); *A61K 2039/5252* (2013.01); *A61K 2039/5254* (2013.01); *A61K 2039/5256* (2013.01); *C12N 2740/16042* (2013.01)

(58) Field of Classification Search
CPC ............ A61K 38/00; A61K 2039/5156; A61K 2039/5252; A61K 2039/5256; A61K 2039/5258; A61K 39/21; A61K 39/12; C12N 2710/10323; C12N 2770/32323; C12N 2770/32334; C12N 15/85; C12N 15/86; C12N 2740/13023; C12N 2740/13034; C12N 2740/15023; C12N 2740/15034; C12N 2740/16043; C12N 2760/16023; C12N 2760/16034; C12N 2760/16134; C12N 2760/16143; Y02A 50/466; C07K 14/705; C07K 16/1063; C07K 2317/622; C07K 14/70564; A61P 31/18; A61P 37/02; A61P 31/14; G01N 33/505; G01N 33/56988

See application file for complete search history.

(56) References Cited

U.S. PATENT DOCUMENTS

| | | | |
|---|---|---|---|
| 7,405,272 B2 * | 7/2008 | Lorenz ............. | C07K 14/70596 530/350 |
| 8,187,872 B2 * | 5/2012 | Allen ........................ | C12N 7/00 435/320.1 |

OTHER PUBLICATIONS

Llewellyn et al. J. Virology, 2013, vol. 87, No. 11, pp. 6441-6454.*
Grover et al. J. Virology, 2015, vol. 89, No. 1, pp. 454-467.*
Grover et al. Journal of Virology, 2015, vol. 2015, vol. 89, vol. 1, pp. 454-467.*
Chukkapolli et al. Journal of Virology, 2008, vol. 82(5). pp. 2405-2417.*
Nurakami et al. PNAS published on Apr. 2020, vol. 117, No. 14, pp. 8055-8063.*

* cited by examiner

*Primary Examiner* — Bao Q Li
(74) *Attorney, Agent, or Firm* — Dave Law Group LLC; Raj S. Dave

(57) ABSTRACT

Embodiments relate to expressing or overexpressing P-selectin glycoprotein ligand-1 (PSGL-1) in human immunodeficiency virus (HIV) producing cells; isolating HIV particles from the HIV producing cells; and preparing the isolated HIV particles as a HIV vaccine. Embodiments relate to a HIV vaccine comprising live attenuated, inactivated, or non-infectious HIV particles. Embodiments relate to systems performing a method comprising administering a vaccine comprising live attenuated, inactivated, or non-infectious HIV particles to a subject in need of the vaccine; and treating or preventing one or more disease states in the subject resulting from HIV infection. Embodiments relate to expressing or overexpressing PSGL-1 in virus producing cells; and inhibiting viral infection; or inhibiting viral spreading; or inactivating viruses and virus producing cells; or producing non-infectious virion particles; or allowing the virus producing cells to produce non-infectious virions, isolating the virions, and preparing non-infectious virions, the virions being HIV particles.

15 Claims, 17 Drawing Sheets
(17 of 17 Drawing Sheet(s) Filed in Color)

FIG. 7a
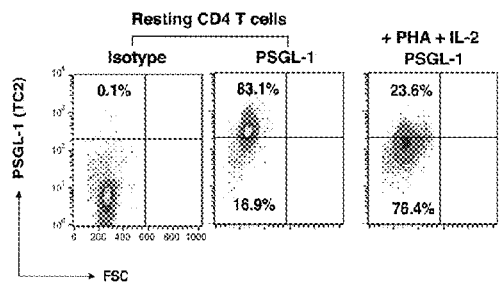
FIG. 7b
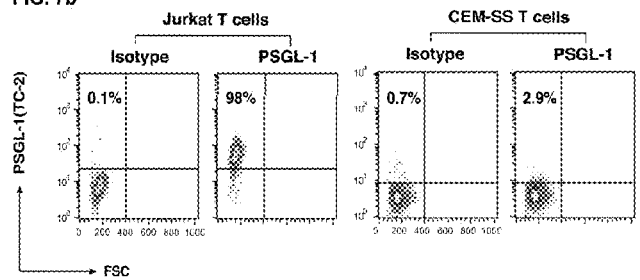
FIG. 7c
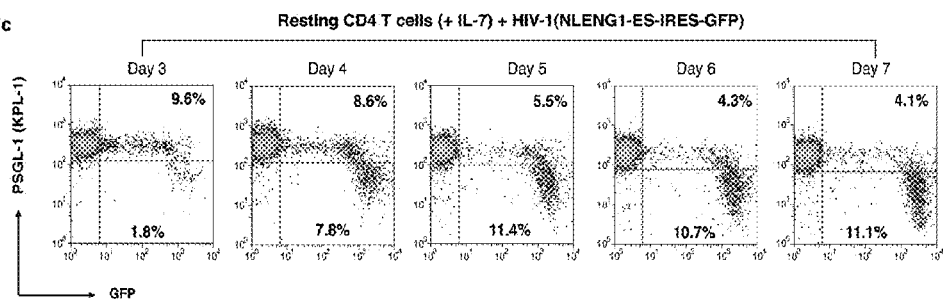
FIG. 7d
FIG. 7e
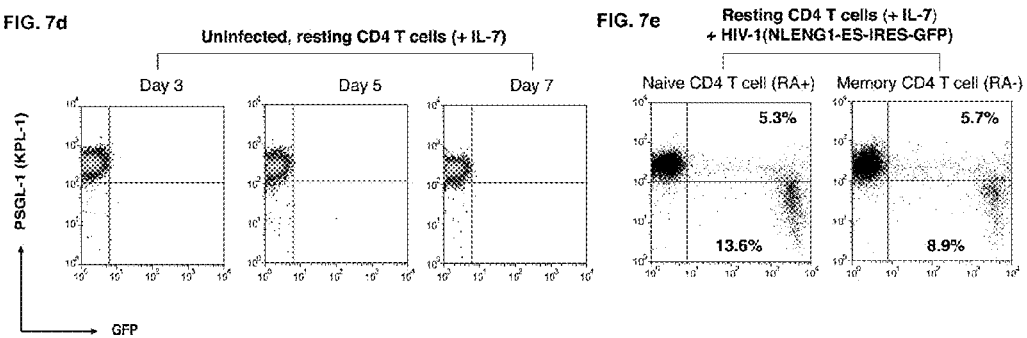

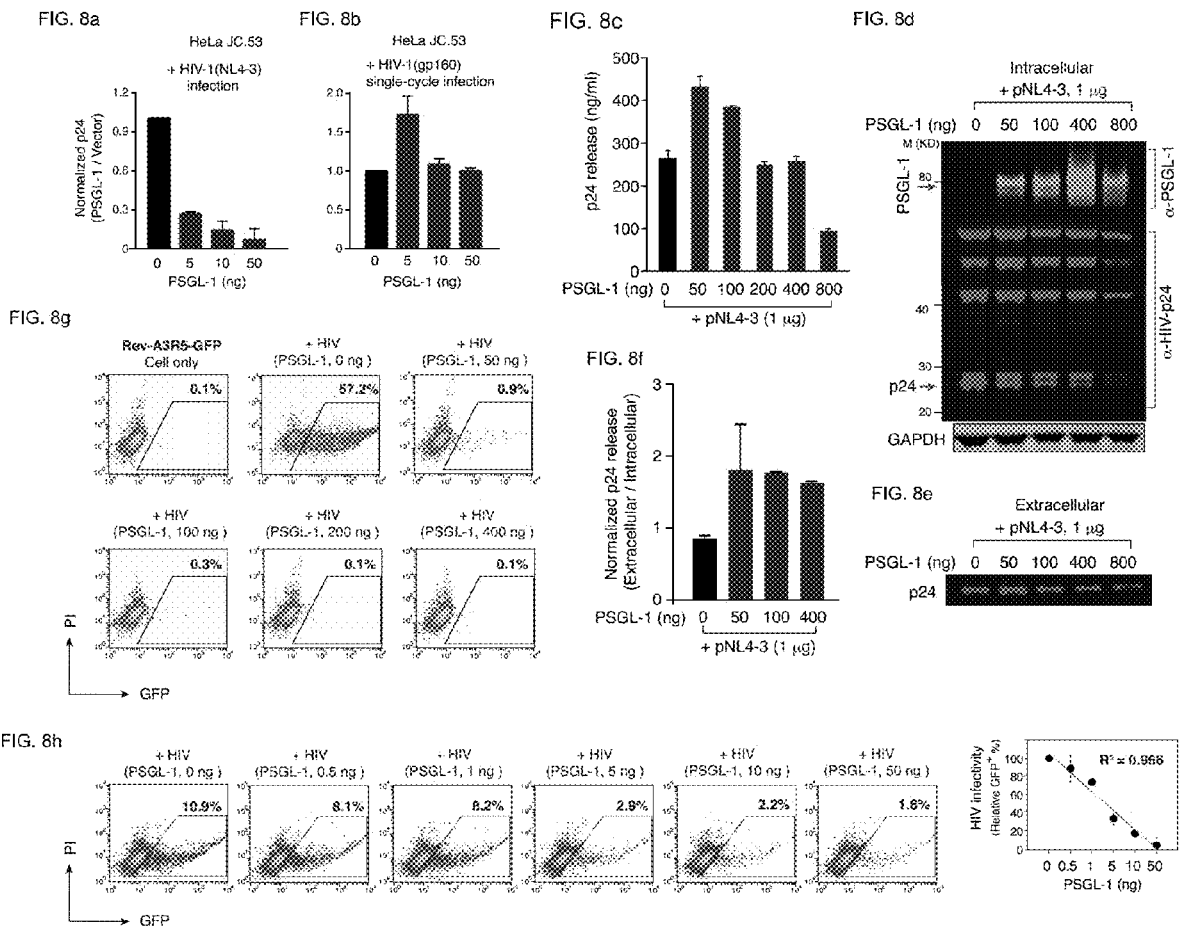

FIG. 9a 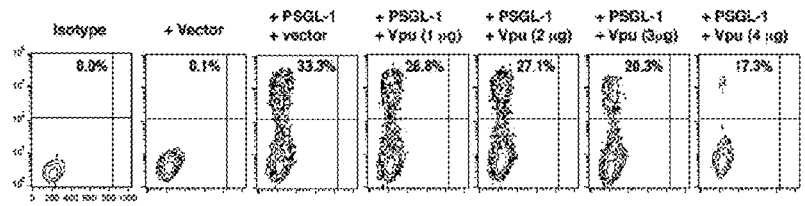 FIG. 9c 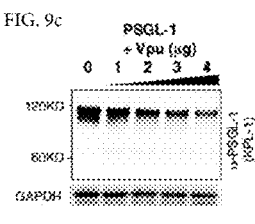
FIG. 9b 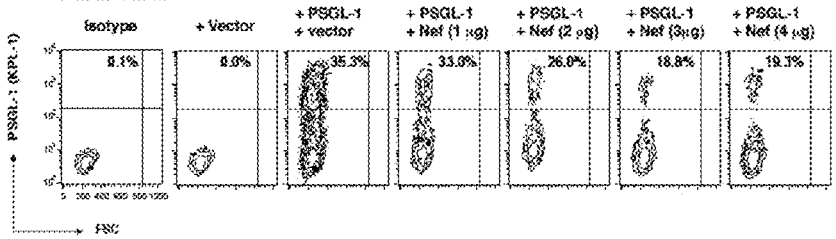 FIG. 9d 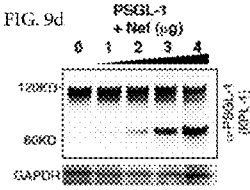

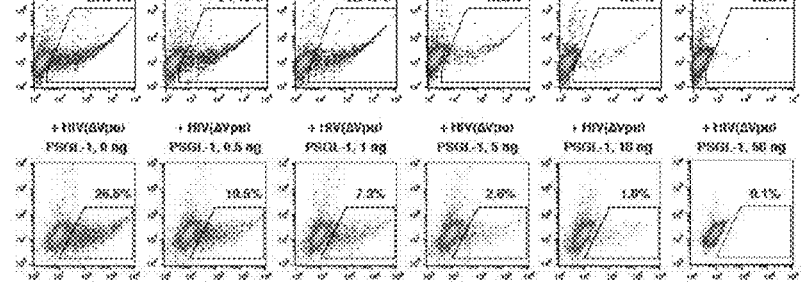
FIG. 9g 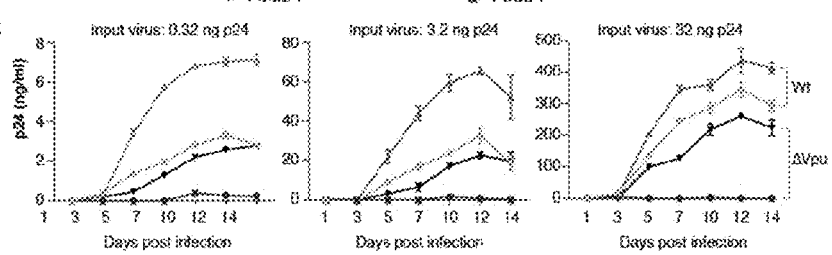 FIG. 9h 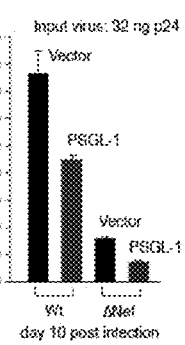

(HIV : PSGL-1 = 1μg : 390 ng)

(HIV : PSGL-1 = 1µg : 390 ng)

METHOD AND SYSTEM FOR INACTIVATING VIRUS INFECTIVITY FOR PRODUCING LIVE-ATTENUATED VACCINES

CROSS-REFERENCE TO RELATED APPLICATIONS

This application claims the benefit under 35 U.S.C. § 119 of U.S. Provisional Application No. 62/628,073, filed Feb. 8, 2018, which is hereby incorporated by reference in its entirety.

FIELD OF THE INVENTION

This invention relates to the process of preparing effective vaccines, especially against viruses such as human immunodeficiency virus (HIV), comprising non-infectious, inactivated, and/or attenuated virion particles. The invention is more particularly concerned with a process involving the expression or overexpression of a protein in a virus producing host cell, such that the virion particles produced are non-infectious, inactivated, and/or attenuated.

BACKGROUND OF INVENTION

An embodiment relates to preparing non-infectious virion particles by using the expression or overexpression of a protein, such as P-selectin glycoprotein ligand-1 (PSGL-1), in virus producing cells to inactivate viral infectivity.

Currently, the preparation of live attenuated viral vaccines frequently requires the inactivation of viral infectivity, resulting in non-infectious virion particles, using chemical and/or biological methods, which have disadvantages. In the case of some viruses, such as HIV, there are no existing methods to prepare live, inactivated, and/or attenuated virus particles for use in vaccines.

Chemical methods for the preparation of inactivated viral vaccines include treating isolated virus or virion particles with chemical substances that tend to destroy the structure of the virus particles, resulting in altered immunogenicity of the virus. Thus, a person vaccinated with a vaccine based on chemically treated virus particles may not produce an immune response effective for the wild type virus. In addition, vaccines produced using chemical treatment of virus particles may be contaminated with chemical impurities that may be harmful to patients.

Biological methods of preparing live attenuated viral vaccines often rely on creating genetically modified or mutant virus particles that have less infectivity than wild type viruses. However, in some instances, such as smallpox, even such attenuated viruses may cause symptoms in subjects due to low-level viral replication, leading to disease states. Such biological methods require specific knowledge of which gene mutations lead to a safe attenuated virus. For some viruses, such as HIV, such knowledge is not available. Thus, currently, there are no biological methods available to produce attenuated strains of HIV.

Until now, the expression or overexpression of proteins, such as PSGL-1, in virus producing cells to isolate virus particles from the virus producing cells and prepare isolated virus particles, such as HIV virus particles, as a virus vaccine has not been used in the preparation of vaccines. Furthermore, such a method has not been used to produce virus particles that are either non-infectious, attenuated, or inactivated. Expression or overexpression of proteins, such as PSGL-1, in virus producing cells has not been used to inhibit viral infection, inhibit viral spreading, inactivate viruses and viral reservoirs, or produce non-infectious virion particles, such as HIV virion particles. The expression or overexpression of PSGL-1 in virus producing cells has not been performed by introducing a vector expressing PSGL-1 into the virus producing cells. Also, a system comprising an HIV vaccine comprising live attenuated, inactivated, or non-infectious HIV particles has not been created. Nor has such a system been created, wherein the HIV particles are produced in virus producing cells, in which PSGL-1 is expressed or overexpressed. Furthermore, such systems have not been used to administer a vaccine to a subject to treat or prevent one or more disease states resulting from HIV infection.

SUMMARY OF INVENTION

An embodiment relates to a method, comprising: expressing P-selectin glycoprotein ligand-1 (PSGL-1) in human immunodeficiency virus (HIV) producing cells; isolating HIV particles from the HIV producing cells; and preparing the isolated HIV particles as a HIV vaccine.

In one embodiment, the HIV particles are non-infectious HIV particles.

In one embodiment, the HIV particles are attenuated HIV particles.

In one embodiment, the HIV particles are inactivated HIV particles.

In one embodiment, the method does not require a chemical that changes a structure of the HIV producing cells.

An embodiment relates to a method, comprising: expressing PSGL-1 in virus producing cells; and inhibiting virus producing cells from producing infectious viruses.

An embodiment relates a method, comprising: expressing PSGL-1 in virus producing cells; and inhibiting viral spreading.

An embodiment relates to a method, comprising: expressing PSGL-1 in virus producing cells; and inactivating viruses.

An embodiment relates to a method, comprising: expressing PSGL-1 in virus producing cells; and producing non-infectious virion particles.

In one embodiment, PSGL-1 is overexpressed in the virus producing cells.

In one embodiment, PSGL-1 is expressed by introducing a vector expressing PSGL-1 into the virus producing cells.

In one embodiment, the virus producing cells produce HIV.

In one embodiment, the virus producing cells are host cells infected with the virus.

In one embodiment, the virus is HIV.

An embodiment relates to a method, comprising: expressing PSGL-1 in virus producing cells; allowing the virus producing cells to produce virions; isolating the virions; and preparing non-infectious virions.

In one embodiment, the virions are HIV particles.

An embodiment relates to a vaccine, comprising: a human immunodeficiency virus (HIV) vaccine comprising live attenuated, inactivated, or non-infectious HIV particles.

An embodiment relates to a vaccine, comprising: a human immunodeficiency virus (HIV) vaccine comprising live attenuated, inactivated, or non-infectious HIV particles, wherein the HIV particles are produced in virus producing cells, and wherein PSGL-1 is expressed in the virus producing cells.

Additional embodiments relate to one or more methods comprising: administering the vaccines claimed herein to a subject in need thereof; and treating or preventing one or more disease states in the subject resulting from HIV infection.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 7a-7e show that HIV-1 infection down-regulates PSGL-1.

FIGS. 8a-8h show that PSGL-1 restricts HIV-1 infectivity when expressed in the virus-producer cell.

FIGS. 9a-9h show that Vpu and Nef antagonize PSGL-1

DETAILED DESCRIPTION

Definitions and General Techniques

Figure 1A:
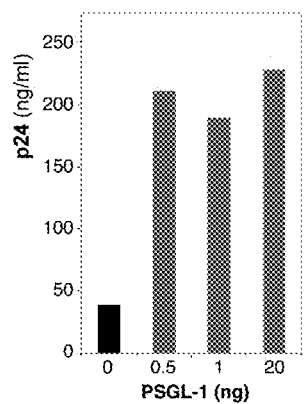
FIGS. 1a-1d show that PSGL-1 promotes HIV-1 virion release.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of virology, immunology, vaccinology, and other related fields described herein are those well-known and commonly used in the art.

The following terms and phrases, unless otherwise indicated, shall be understood to have the following meanings.

The term PSGL-1 as used herein refers to P-selectin glycoprotein ligand-1, which is a membrane protein that mediates the surface tethering and rolling of Th1 T cells for tissue migration, and has been suggested to be up-regulated by Th1 cytokines such as interferon gamma. PSGL-1, also known as SELPLG or CD162, is primarily expressed on the surface of lymphoid and myeloid cells and binds to all three members of the selectin family of proteins, P-, E-, and L-selectin. PSGL-1 is up-regulated during inflammation to mediate leukocyte tethering and rolling on the surface of the endothelium to promote leukocyte migration into inflamed tissues. In a mouse model of chronic viral infection, PSGL-1 has been reported to be an immune factor regulating T-cell checkpoints. In addition, PSGL-1 serves as a receptor for enterovirus 71 (EV71) infection of leukocytes. PSGL-1 has also been shown to be an INF-γ-regulated factor involved in Th1-mediated antiviral activity. During T-cell differentiation, culturing T cells in the Th1 cytokine INF-γ and IL-12 promoted PSGL-1 expression preferentially in the INF-γ-producing T-cell population, suggesting that PSGL-1 could be an INF-γ-regulated factor involved in Th1-mediated antiviral activity. PSGL-1 was reported to co-cluster with HIV-1 Gag at sites of assembly in the T-cell uropod.

The term virus or virion as used herein refers to a submicroscopic infectious agent that is unable to grow or reproduce outside a host cell. It is non-cellular but consisting of a core of DNA or RNA surrounded by a protein coat. A virus is a small parasite that cannot reproduce by itself. Once it infects a susceptible cell, however, a virus can direct the cell machinery to produce more viruses. Virus and virion as used herein are synonymous.

The phrase virus particle or virion particle as used herein refers to a complete infectious agent that consists of an RNA or DNA core with a protein coat sometimes with external envelopes and that is the extracellular infective form of a virus.

The phrase native structure of an isolated HIV particle as used herein refers to the naturally occurring three-dimensional structure of an HIV particle, as encoded by the genetic material of the virus.

The term HIV as used herein refers to human immunodeficiency virus. Infection of subjects with HIV can result in diseases, including acquired immune deficiency syndrome (AIDS).

The term subject as used herein refers to a human individual. This individual could be a patient requiring prophylaxis and/or medical treatment.

The phrase virus producing cell as used herein refers to cell that a virus has infected and whose cell machinery the virus can direct to produce more viruses.

The phrase expressing or overexpressing PSGL-1 in virus producing cells as used herein refers to causing the protein PSGL-1 to be synthesized by the cell in larger quantities than would normally be expressed by the cell on its own.

The phrase isolating HIV particles as used herein refers to separating HIV particles from other substances, such as the components of the virus producing host cell, using methods such as chromatography.

The phrase non-infectious virus particle as used herein refers to a virus particle that has been rendered unable to infect a host cell and cause one or more effects, such as disease or death of the host cell.

The phrase attenuated virus particle as used herein refers to a virus particle that has been weakened in its ability to infect a host cell and cause one or more effects, such as disease or death of the host cell.

The phrase inactivated virus particle as used herein refers to a virus particle that has been rendered unable to infect a host cell and cause one or more effects, such as disease or death of the host cell.

The phrase inhibiting viral infection as used herein refers to decreasing somewhat or fully the ability of a virus to infect a host cell and cause one or more effects, such as disease or death of the host cell.

The phrase inhibiting viral spreading as used herein refers to decreasing somewhat or fully the production of more viruses either within our outside of a cell or organism.

The phrase inactivating viruses as used herein refers to rendering viruses unable to cause one or more effects in a host cell, such as disease or death of the host cell.

The phrase producing non-infectious virion particles as used herein refers to creating a virus that is unable to infect a host cell and cause one or more effects in the cell, such as disease or death of the host cell.

The phrase introducing a vector as used herein refers to the process of causing a cell to take up a piece of genetic material, often foreign to the cell.

The phrase host cell as used herein refers to a cell which a virus infects to reproduce itself, because a virus is a small parasite that cannot reproduce by itself.

The phrase host cells infected with the virus as used herein refers to a host cell that has been affected in its normal functioning by the attachment and/or internalization of a virus.

The phrase disease state as used herein refers to a disorder of structure or function of a human caused by a virus.

The phrase allowing a virus producing cell to produce virions as used herein refers to enabling a cell to complete the process of a virus directing the cell's machinery to reproduce the virus fully.

An embodiment makes it possible to express or overexpress P-selectin glycoprotein ligand-1 (PSGL-1) in human immunodeficiency virus (HIV) producing cells; isolate HIV particles from the HIV producing cells; and prepare the isolated HIV particles as a HIV vaccine.

In another aspect, an embodiment features a system comprising a human immunodeficiency virus (HIV) vaccine comprising live attenuated, inactivated, or non-infectious HIV particles.

Yet another embodiment features a system comprising a human immunodeficiency virus (HIV) vaccine comprising live attenuated, inactivated, or non-infectious HIV particles, wherein the HIV particles are produced in virus producing cells, and wherein PSGL-1 is expressed or overexpressed in the virus producing cells. Furthermore, the system does not require a chemical that destroy a structure of the HIV producing cells.

An embodiment relates to a system capable of performing a method comprising administering a vaccine comprising live attenuated, inactivated, or non-infectious HIV particles to a subject in need of the vaccine; and treating or preventing one or more disease states in the subject resulting from HIV infection.

An embodiment relates to a system capable of performing a method comprising administering a vaccine comprising live attenuated, inactivated, or non-infectious HIV particles, wherein the HIV particles are produced in virus producing cells, and wherein PSGL-1 is expressed or overexpressed in the virus producing cells, to a subject in need of the vaccine; and treating or preventing one or more disease states in the subject resulting from HIV infection.

Yet another embodiment relates to a method, comprising expressing or overexpressing PSGL-1 in HIV producing cells; isolating HIV particles from the HIV producing cells; and preparing the isolated HIV particles as a HIV vaccine. The HIV particles may be non-infectious, attenuated, or inactivated. Furthermore, the method does not require a chemical that destroy a structure of the HIV producing cells.

Another embodiment relates to a method, comprising expressing or overexpressing PSGL-1 in virus producing cells; and inhibiting viral infection, or inhibiting viral spreading, or inactivating viruses and virus producing cells, or producing non-infectious virion particles.

A variation of the embodiment described immediately above is expressing or overexpressing PSGL-1 by introducing a vector expressing PSGL-1 into the virus producing cells.

Another embodiment relates to a method, comprising expressing or overexpressing PSGL-1 in virus producing cells; and inhibiting viral infection, or inhibiting viral spreading, or inactivating viruses, or producing non-infectious virion particles, wherein the virus producing cells produce HIV, or wherein the virus producing host cells are host cells infected with the virus, or wherein the virus producing host cells are host cells infected with the HIV virus.

Yet another embodiment relates to a method, comprising expressing or overexpressing PSGL-1 in virus producing cells; allowing the virus producing cells to produce non-infectious viral particles; isolating the virions; and preparing non-infectious virions. These virions could be HIV particles.

In one embodiment PSGL-1 restricts HIV infection through a novel "kill and release" mechanism, overexpression of PSGL-1 promotes virion release, and the released virions lose infectivity. PSGL-1 restricts HIV spreading through direct virion incorporation, which inactivates progeny virion attachment and entry into CD4 T cells. PSGL-1 restricts HIV infection through promoting the release of non-infectious virion particles. Given that the released virion particles are not able to attach to target cells, these particles are likely endocytosed by antigen presenting cells, and processed as antigens for MHC class II antigen presentation to stimulate anti-viral humoral immunity.

In another embodiment PSGL-1 inhibits the infectivity of VSV-G pseudo-typed lentiviruses, demonstrating that PSLG-1 potentially has broad anti-viral activity against different viruses. PSGL-1 can be used to inactivate viral infectivity for producing live-attenuated viral vaccines.

In another embodiment PSGL-1 restricts HIV infection through promoting the release of non-infectious virion particles. Given that the released non-infectious virion particles are not able to attach to target CD4 T cells, these particles are likely endocytosed by antigen presenting cells, and processed as antigens for MHC class II antigen presentation to stimulate anti-HIV humoral immunity.

In another embodiment PSGL-1 promotes the release of non-infectious virions ("kill and release"). The inactivation by PSGL-1 of virion infectivity may occur through blocking the protease processing of virion proteins. Some of the most abundant cellular proteins in the virion particles are actin and cofilin (10-15% and 2-10% of gag). HIV reverse transcriptase, nuclear capsid, and Nef have been shown to bind to actin directly. It is possible that F-actin may serve as a scuffled protein to organize the proper positioning of various virion proteins and their precursors. PSGL-1 may interfere with the organization of virion proteins and affect their proper processing by protease.

In yet another embodiment PSGL-1 (P-selectin glycoprotein ligand-1) is a dimeric, mucin-like, 120-kDa glycoprotein that binds to P-, E-, and L-selectins. PSGL-1 is primarily expressed on the surface of lymphoid and myeloid cells and is up-regulated during inflammation to mediate leukocyte tethering and rolling on the surface of the endothelium for migration into inflamed tissues. The presence of high levels of PSGL-1 on T cells potently restricts HIV-1 infectivity; reducing the attachment of virions to target cells and impairing infectivity in both single-round and spreading infections. PSGL-1 is itself incorporated into HIV-1 particles. HIV-1 infection, and expression of Vpu and Nef, downregulate PSGL-1 from the cell surface, enabling the virus to antagonize PSGL-1-mediated restriction.

In another embodiment PSGL-1, also known as SELPLG or CD162, is primarily expressed on the surface of lymphoid and myeloid cells and binds to all three members of the selectin family of proteins, P-, E-, and L-selectin. PSGL-1 mediates leukocyte tethering and rolling on the surface of endothelium to promote leukocyte migration into inflamed tissues. In a mouse model of chronic viral infection, PSGL-1 is an immune factor regulating T-cell checkpoints. In addition, PSGL-1 serves as a receptor for enterovirus 71 (EV71) infection of leukocytes.

In one embodiment PSGL-1 is an INF-γ-regulated factor involved in Th1-mediated antiviral activity. During T-cell differentiation, culturing T cells in the Th1 cytokine INF-γ and IL-12 promotes PSGL-1 expression preferentially in the INF-γ-producing T-cell population, suggesting that PSGL-1 could be an INF-γ-regulated factor involved in Th1-mediated antiviral activity. PSGL-1 co-clusters with HIV-1 Gag at sites of assembly in the T-cell uropod.

In another embodiment PSGL-1, a mucin-like glycoprotein highly expressed on blood resting CD4 T cells, restricts HIV-1 virion infectivity. In this respect, PSGL-1-mediated restriction resembles that imposed by the Apobec3G, SERINC5, MARCH, GBP5, and 90K proteins, which also target virion infectivity. In contrast to the Vpu-antagonized restriction factor BST2/tetherin that tethers virion particles to the cell surface, PSGL-1 does not inhibit virion release. However, PSGL-1-imprinted virions lose the ability to attach to, and infect, target cells. PSGL-1 is a remarkably potent inhibitor of HIV-1 infectivity; it almost completely inactivated WT HIV-1 particle infectivity at a vector-to-proviral DNA ratio of 0.05:1 (FIG. 8e and FIG. 8f). Given this high potency, it appears that HIV-1 uses two of its accessory proteins, Vpu and Nef, to antagonize PSGL-1.

One of the embodiments provides novel insights into the ability of the host cell to interfere with HIV-1 infection, and the biological function of lentiviral accessory proteins. Further elucidation of the mechanism by which PSGL-1 restricts HIV-1 infection may offer new therapeutic strategies for targeting HIV-1 replication.

The disclosed embodiments change the way in which vaccines comprising live attenuated, inactivated, or non-infectious virion particles, such as HIV particles, are produced.

Figure 1B:
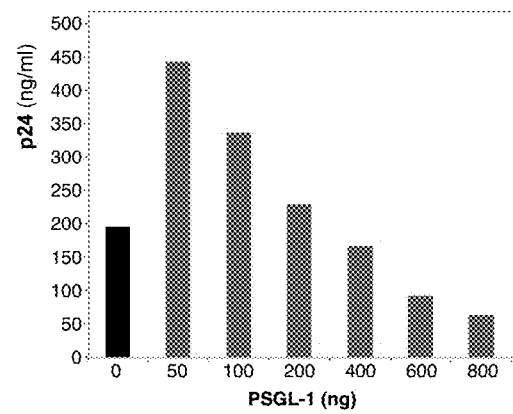
Figure 1C:
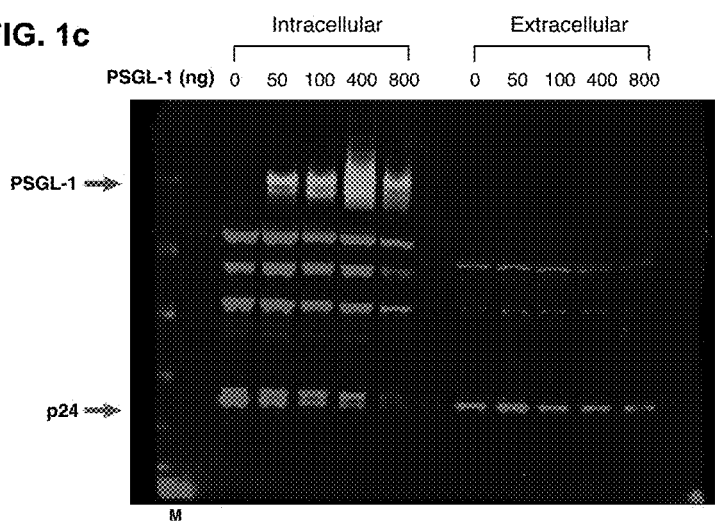
Figure 1D:
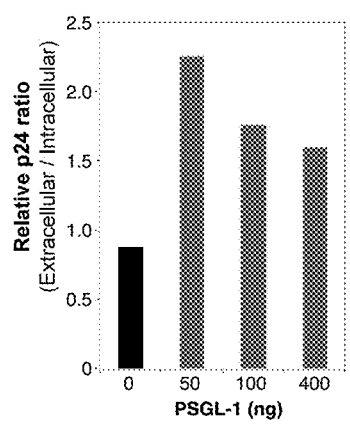

FIGS. 1a-1d illustrates that PSGL-1 promotes HIV-1 virion release. To determine possible effects of PSGL-1 expression on HIV infection, HEK293T cells were cotransfected with HIV(NL4-3) DNA (1000 ng) plus a PSGL-1 expressing vector, using a range of vector dosages from 0.5 to 800 ng. At low dosages (0.5 to 50 ng), PSGL-1 greatly promoted virion release (200 to 400% based on p24). At higher dosages (50 ng and above), the enhancement of virion release was decreased. The empty vector DNA was added during transfection to maintain the same amount of DNA used for cotransfection. (FIGS. 1a and 1b). However, when intracellular viral proteins were examined, PSGL-1 was found to inhibit intracellular p24 accumulation at dosages higher than 50 ng, and 800 ng PSGL-1 was toxic to cells. Cotransfected cells and extracellular virion particles were lyszed and analyzed by SDS-PAGE and western blot using an anti-PSGL-1 antibody and an anti-HIV antibody. (FIG. 1c). When normalized to intracellular p24, PSGL-1 enhanced virion release at all non-toxic dosages tested. The relative ratio of p24 on the western blot was quantified (extracellular p24/intracellular p24). (FIG. 1d). These results appear to be consistent with an earlier report that PSGL-1 is involved in HIV assembly and budding. It is possible that increasing the amount of PSGL-1 to the sites of HIV assembly promotes virion release.

Figure 2A:
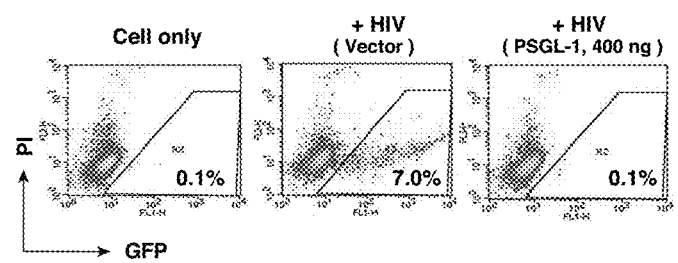
FIGS. 2a-2c show that PSGL-1 promotes the release of non-infectious virion particles.
Figure 2B:
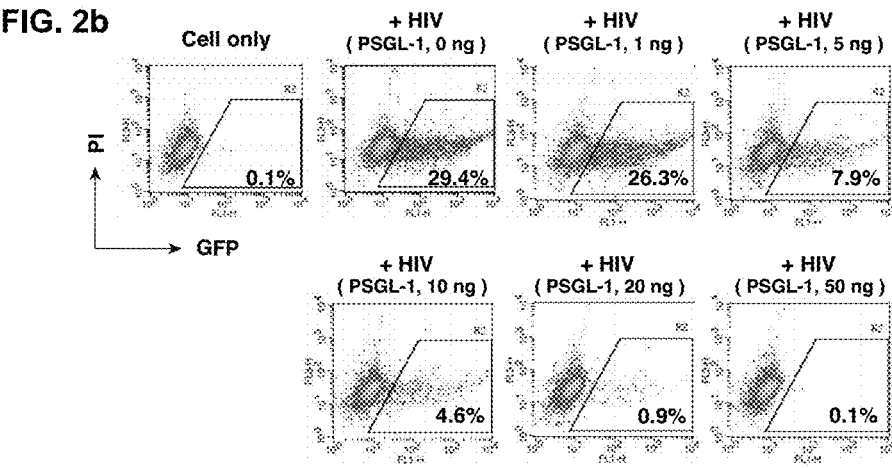
Figure 2C:
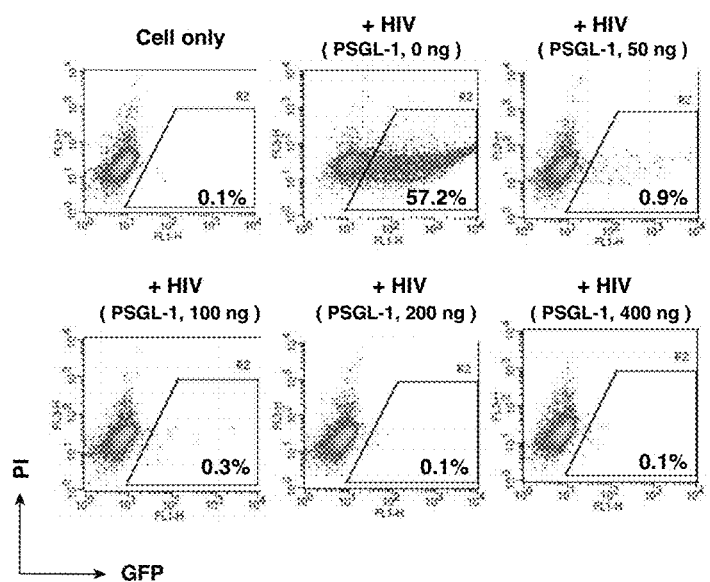

FIGS. 2a-2c illustrate that PSGL-1 promotes the release of non-infectious virion particles. The infectivity of the released virion to infect target CD4 T cells was examined using an HIV Rev-dependent GFP reporter cell line, A3R5-GFP-RRE. Unlike LTR-driving reporter cells, the Rev-dependent report cell strictly requires HIV Rev to turn on GFP expression, which is not affected by cellular factors present in the supernatant of transfected HEK293T cells. Surprisingly, while PSGL-1 promotes virion release, the particles released completely lost infectivity at PSGL-1 vector dosages of 50 ng and higher (HIV: PSGL-1 vector ratio, 1:0.05). HIV particles are also partially inactivated by PSGL-1 at dosages as low as 1-5 ng, and there is a dosage-dependent inactivation of HIV by PSGL-1 at dosages between 1 to 50 ng. HEK293T cells were cotransfected with HIV(NL4-3)DNA (1 ug) plus 400 ng of PSGL-1 expressing vector (PSGL-1). The empty vector DNA (vector) was added during transfection to maintain the same amount of DNA used for cotransfection. At 48 hours post co-transfection, virion particles were harvested and used to infect an HIV Revdependent reporter cells A3R5-GFP-RRE. GFP expression was quantified at 48 hours post infection. An equal p24 level of p24 was used for infection (FIGS. 2a and 2c). Cotransfection and infection were done as in FIG. 2a) and FIG. 2c). An equal volume of viruses were used the infection of A3R5-GFP-RRE (FIG. 2b).

Figure 3A:
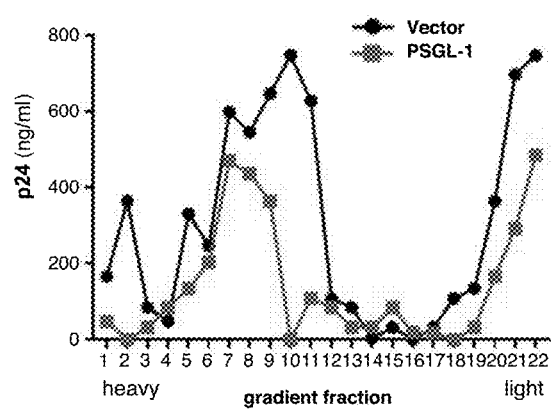
FIGS. 3a-3c show that PSGL-1 is incorporated into virion particles.
Figure 3B:
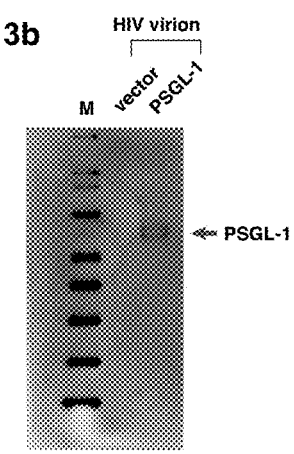
Figure 3C:
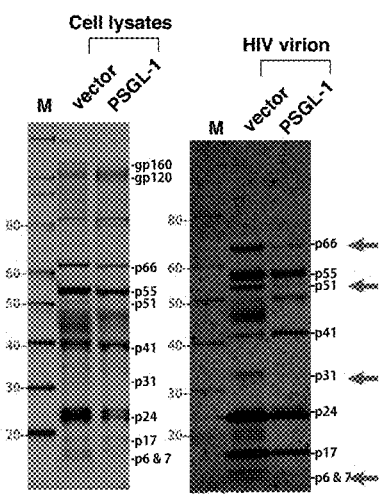

FIG. 3 illustrates that PSGL-1 is incorporated into virion particles. To determine whether PSGL-1 is incorporated into HIV virion particles, we cotransfected HIV(NL4-3) DNA with the PSGL-1 vector, and purified the virion particles by 2 rounds of high-speed centrifugation, through a gradient of 6-18% OpiPrep solution. HEK293T cells were cotransfected with HIV(NL4-3)DNA (1 ug) plus 200 ng of a PSGL-1 expressing vector (PSGL-1). The empty vector DNA (vector) was added during transfection to maintain the same amount of DNA used for cotransfection. Virions were harvested at 48 hours post cotranfection and purified by ultra-speed centrifugation in OptiPrep gradient solution (1.2-18%). (FIG. 3a). Highly purified virion pellets were analyzed by SDS-PAGE Western blot using an anti-PSGL-1 antibody. As shown in FIG. 3b, we detected the presence of PSGL-1 in virion particles when the blot was probed with an anti-PSGL-1 antibody. In addition, we also probed the blot with anti-HIV antibodies, and detected the presence of various virion proteins. However, the relative ratios of virion proteins were altered. The pol p66/p51/p31, and the p6/p7 proteins were diminished. Virion pellets were analyzed by SDS-PAGE and anti-HIV anti-serum (FIG. 3c). These results suggest that the incorporation of PSGL-1 may affect the intravirion protease cleavage of virion polyproteins, particularly the gag-pol precursors, which may block the maturation of released virion particles.

Figure 4A:
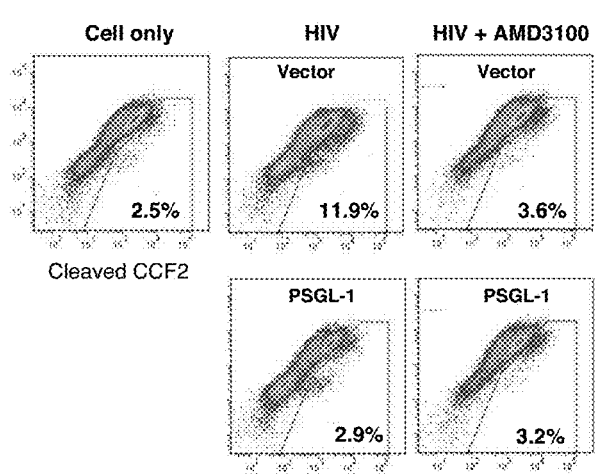
FIGS. 4a-4b shows that virion incorporation of PSGL-1 prevents virion attachment and entry.
Figure 4B:
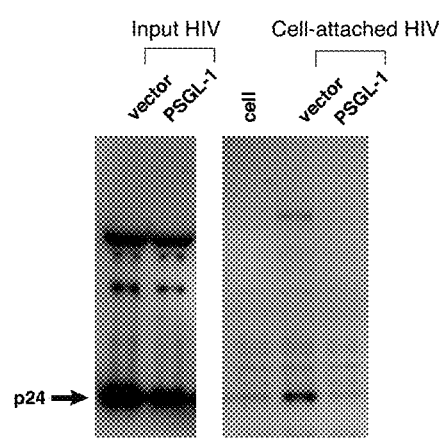

FIGS. 4a-4b illustrate that virion incorporation of PSGL-1 prevents virion attachment and entry. The mechanism of PSGL-1-mediated inactivation of virion infectivity was further studied by following the early steps of HIV infection. Using an HIV entry assay, the BlaM-Vpr assay, it was observed that the virions produced from PSGL-1 vectorcotransfected cells were not able to enter CD4 T cells, suggesting that virion incorporation of PSGL-1 may affect virion attachment or virus-cell fusion. HEK293T cells were cotransfected with HIV(NL4-3)DNA (1 ug) plus 200 ng of a PSGL-1 expressing vector (PSGL-1). The empty vector DNA (vector) was added during transfection to maintain the same amount of DNA used for cotransfection. Virions were harvested at 48 hours post cotranfection and used to perform a BlaM-Vprbased HIV entry assay. AMD3100 was used as a control (FIG. 4a). A virion attachment assay was also performed, and it was observed that the virions produced from PSGL-1 vector-cotransfected cells were not able to attach to HIV target cells. Virions were also used to perform a virus attachment assay. Viruses were incubated with target CD4+CXCR4+JC.53 cells at 4 degree for 2 hours. Cells were extensively washed, lyzed, and analyzed by SDS-PAGE and western blot using an anti-HIV p24 antibody. The input viruses used for the attachment assay were also analyzed. (FIG. 4b).

Figure 5:
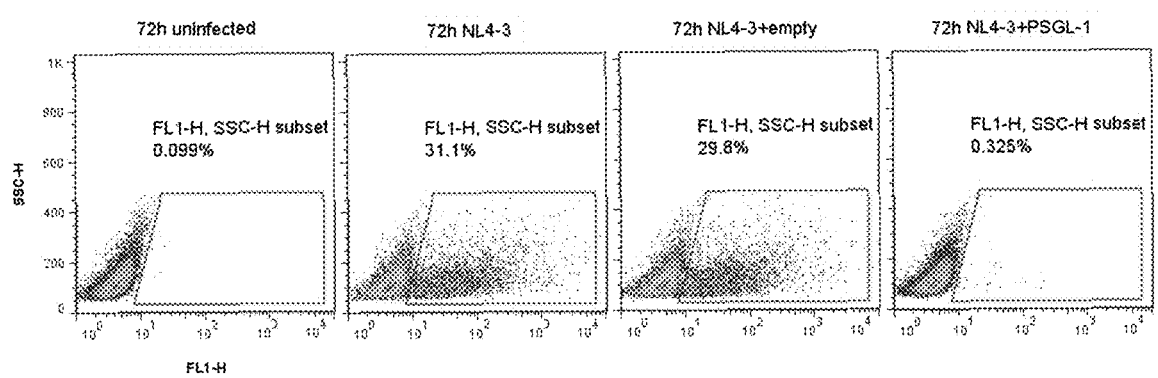
FIG. 5 shows that PSGL-1 also inhibits viral entry through the endocytotic pathway.

FIG. 5 illustrates that PSGL-1 also blocks the infectivity of VSV-G pseudo-typed HIV virion particles and inhibits viral entry through the endocytotic pathway. It was investigated whether PSGL-1-mediated inhibition of viral entry is specific to the HIV envelope-mediated plasma membrane fusion. HIV was pseudo-typed with the VSV-G envelope (vesicular stomatitis virus glycoprotein), which mediates viral entry through endocytosis rather than member fusion. As shown in FIG. 5, the inhibition of VSV-G pseudo-typed HIV infection was observed, demonstrating that PSGL-1 can block viral entry through both plasma member fusion and endocytosis. PSGL-1 is expected to block the infectivity of multiple viruses. HEK293T cells were cotransfected with HIV(KFS)+pCMV-VSV-G DNA plus a PSGL-1 expressing vector (PSGL-1) or the empty vector DNA (Empty). At 48 hours post co-transfection, virion particles were harvested and used to infect an HIV Rev-dependent reporter cells A3R5-GFP-RRE. GFP expression was quantified at 48 hours post infection.

Figure 6A:
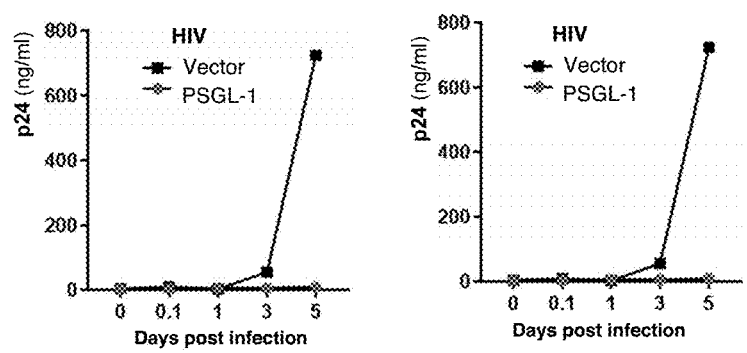
FIGS. 6a-6b show that PSGL-1 inactivates HIV infectivity.
Figure 6B:
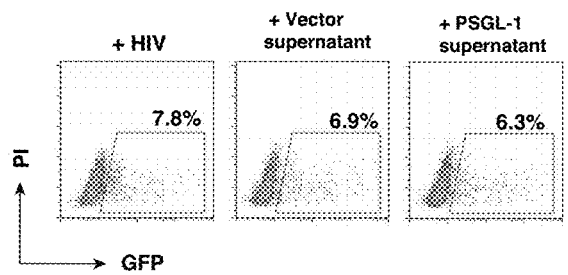

FIGS. 6a-6b illustrate that PSGL-1 inactivates HIV infectivity. HEK293T cells were cotransfected with HIV(NL4-3)DNA (1 ug) plus 200 ng of a PSGL-1 expressing vector (PSGL-1) or the empty vector (Vector). At 48 hours post cotransfection, virion particles were harvested and used to infect A3R5.7 CD4 T cells or A3R5-GFP-RRE. An equal p24 level of p24 was used for infection. Viral replication was monitored by p24 release (FIG. 6a). PSGL-1 tranfection supernatant did not inhibit HIV infection. HEK293T cells were transfected with 200 ng of a PSGL-1 expressing vector (PSGL-1) or the empty vector (Vector). Supernatants were harvested at 48 hours, and 400 ul of the supernatants were mixed with 200 ul of HIV-1(NL4-3) virion particles, and then used to infect A3R5-GFP-RRE. For control, 400 ul fresh medium was mixed with HIV (FIG. 6b). The complete inactivation of HIV infectivity was confirmed by quantifying HIV spreading infection in A3R5 CD4 T cells by p24 release This inactivation of HIV infectivity was not caused by possible cellular factors present in the cotransfection supernatant; the supernatant from PSGL-1 vector-only transfected cells did not inhibit HIV infectivity when mixed with HIV virion particles. Given that PSGL-1 is a membrane protein and is recruited to the sites of virion assembly, it is possible that PSGL-1 may inactivate virion infectivity through direct incorporation into virion particles.

FIGS. 7a-7e illustrates that HIV-1 infection down-regulates PSGL-1. (FIG. 7a) Blood resting CD4 T cells were purified by negative selection, activated with PHA+IL-2, or left unstimulated. Cell surface PSGL-1 expression was analyzed by flow cytometry. (FIG. 7b) Jurkat and CEM-SS cells were similarly stained for surface PSGL-1. (FIG. 7c) Blood resting CD4 T cells were infected with NLHG1-ES-IRES-GFP reporter virus (125 to 320 ng p24 per million cells). Following infection, cells were washed and cultured in complete medium plus IL-7 (2 ng/ml) to permit low-level viral replication. Surface PSGL-1 expression was analyzed at the indicated days. Shown are the percentages of the GFP+ or GFP– cells with low or high PSGL-1 staining in each panel. PSGL-1 down-regulation was observed only in the HIV+/GFP+ cell population. (FIG. 7d) For controls, uninfected cells were similarly cultured in IL-7 and surface PSGL-1 expression was analyzed at the indicated days. Culturing resting CD4 T cells in IL-7 did not lead to PSGL-1 downregulation. (FIG. 7e), Cells were also stained for surface PSGL-1 expression on the CD45RA+(naïve) and CD45RA– (memory) CD4 T cells at day 7, and analyzed by flow cytometry.

FIGS. 8a-8h illustrates that PSGL-1 restricts HIV-1 infectivity when expressed in the virus-producer cell. (FIG. 8a and FIG. 8b) HeLa JC.53 cells were transfected with a PSGL-1 vector or a control empty vector for 48 hours, and then infected with HIV-1(NL4-3) for spreading infection (FIG. 8a) or HIV-1(gp160) for single-round infection (FIG. 8b). Viral replication was quantified by p24 release at 72 hours (FIG. 8a) or 48 hours for (FIG. 8b). (FIGS. 8c to 8f) HEK293T cells were cotransfected with HIV(NL4-3) DNA (1 μg) plus different amounts of PSGL-1 expression vector. Viral p24 release was quantified at 48 hours (FIG. 8c). Cells were also lysed and analyzed by western blot for intracellular PSGL-1 and HIV-1 proteins (FIG. 8d). Extracellular virion p24 was also analyzed by western blot (FIG. 8e), and the relative ratio of extracellular and intracellular p24 was plotted (FIG. 8f). (FIG. 8g and FIG. 8h) Virions released from HEK293T cells cotransfected with HIV(NL4-3) DNA (1 μg) plus PSGL-1 DNA (0.5 to 400 ng) were harvested and normalized for p24, and viral infectivity was quantified by infecting the T-cell line-derived Rev-A3R5-GFP indicator cells. HIV-1 replication was quantified by GFP expression. Shown are the percentages of GFP+ cells at 48-72 hours postinfection. The PSGL-1 dose-dependent inhibition curve in (FIG. 8h) was plotted using results from 3 independent experiments.

Figure 9E:
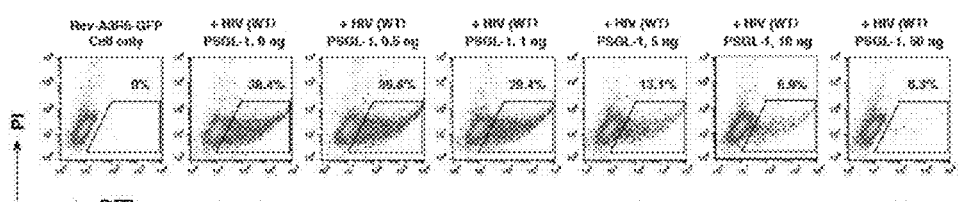
Figure 9F:
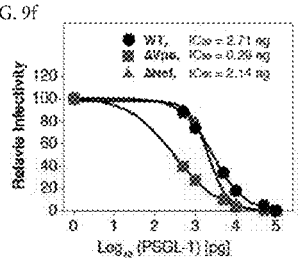

FIGS. 9a-9h illustrates that Vpu and Nef antagonize PSGL-1. (FIG. 9a and FIG. 9b) Downregulation of PSGL-1 from the cell surface by Vpu and Nef. HEK293T cells were cotransfected with PSGL-1 (100 ng) and a Vpu (FIG. 9a), or Nef (FIG. 9b) expression vector at various DNA inputs. Surface PSGL-1 expression was quantified and shown as the percentages of cells expressing PSGL-1. For controls, an empty vector was used (+Vector). The same amount of DNA was used in all transfections. (FIG. 9c and FIG. 9d) Levels of intracellular PSGL-1 in Vpu- or Nef-cotransfected cells were quantified by western blot at 48 hours post-cotransfection. (FIG. 9e and FIG. 9f) Vpu and Nef antagonize PSG1-1. HEK293T cells were cotransfected with various amounts of PSGL-1 DNA (0.5-50 ng) plus 1 μg HIV(NL4-3) WT, HIV(ΔVpu), or HIVΔNef DNA. Virions were harvested and used to infect Rev-A3R5-GFP indicator cells. GFP expression was quantified and shown as the percentage of GFP+ cells at 72 hours postinfection. (FIG. 9g and FIG. 9h) HeLa JC.53 cells were stably transfected with PSGL-1 or empty vector DNA and drug-selected to obtain stably transfected cells. Cells were then infected with 3 different inputs of HIV-1(NL4-3)WT, HIV-1(ΔVpu) (FIG. 9g), or HIV-1 (ΔNef) (FIG. 9h). Viral replication was quantified by p24 release. For (FIG. 9h), only the data for 32 ng p24 input at day 10 are shown.

Figure 10A:
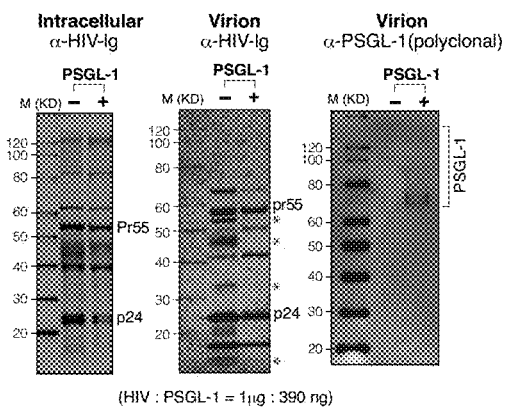
FIGS. 10a-10c show that PSGL-1 is incorporated into virions and its expression and incorporation alters viral protein composition in virion.
Figure 10C:
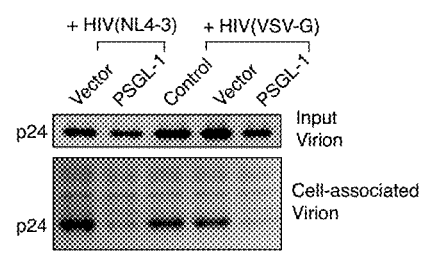
Figure 10B:
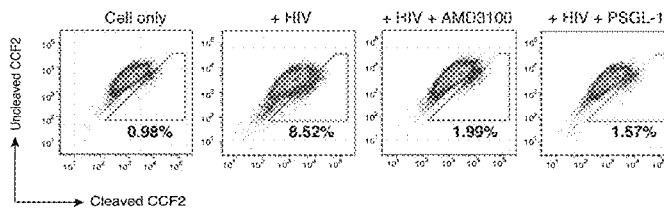

FIGS. 10a-10c illustrate that PSGL-1 is incorporated into virions and its expression alters viral protein composition in virion particles. (FIG. 10a) HEK293T cells were cotransfected with PSGL-1 DNA plus HIV-1(NL4-3). Virion particles were harvested at 48 hours post-cotransfection, and intracellular and virion proteins were analyzed by western blot using antibodies against PSGL-1 (polyclonal) or HIV proteins (anti-HIV serum). The red stars highlight the severe reductions in protein levels in in virions produced from PSGL-1-expressing cells. Positions of the Gag precursor protein (pr55) and p24 (CA) are indicated. (FIG. 10b) Virions produced from HEK293T cells cotransfected with PSGL-1 expression vector plus HIV-1(NL4-3) were used for an entry assay. As controls, HIV-1 virions similarly produced in the presence of an empty vector were used. Equal p24 was used for the assay. The entry inhibitor AMD3100 was also used as a control to block virus entry. The percentages of cells with cleaved CCF2 are shown. FIG. 10c, Virion particles produced in the presence of PSGL-1 or the empty vector were assayed for attachment to target HeLa JC.53 cells at 4° C. for 2 hours. Cells were washed and then analyzed by western blot for cell-associated p24.

Figure 11A:
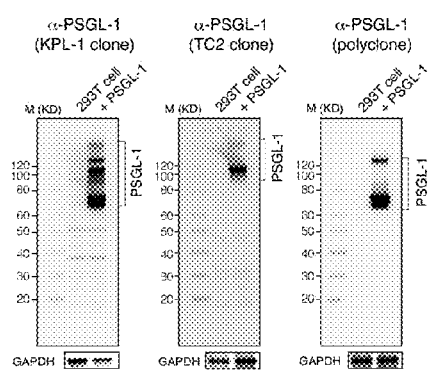
FIG. 11a-11c shows validation of PSGL-1 expression following transfection of HEK293T and HeLa JC.53 cells.
Figure 11C:
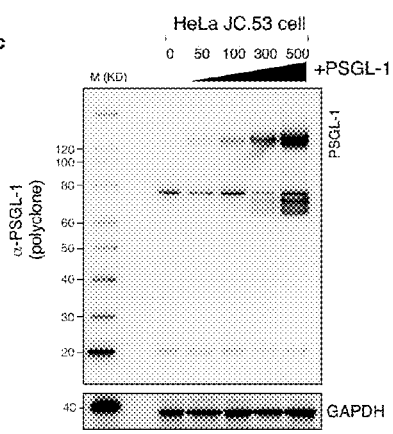
Figure 11B:
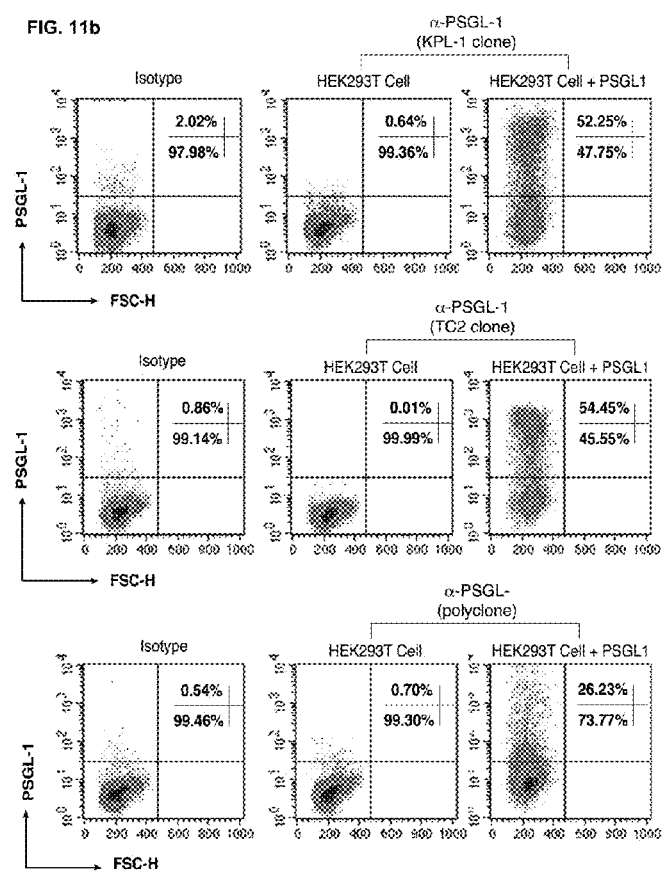

FIGS. 11a-11c illustrate the Validation of PSGL-1 expression following transfection of HEK293T and HeLa JC.53 cells. (FIG. 11a and FIG. 11b), HEK293T cells were transfected with a PSGL-1 expression vector (pCMV-PSGL-1), and then analyzed by western blot using 3 different commercial antibodies (FIG. 11a). Expression of PSGL-1 on the surface was analyzed by surface staining and flow cytometry. Shown are the percentages of cells with high or low PSGL-1 staining in each panel. (FIG. 11c) HeLa JC.53 cells were transfected with pCMV-PSGL-1 at the indicated inputs (ng). PSGL1 expression was analyzed by western blot at 48 hours posttransfection using anti-PSGL-1 polyclonal antibodies. GAPDH was similarly analyzed as a loading control.

Figure 12:
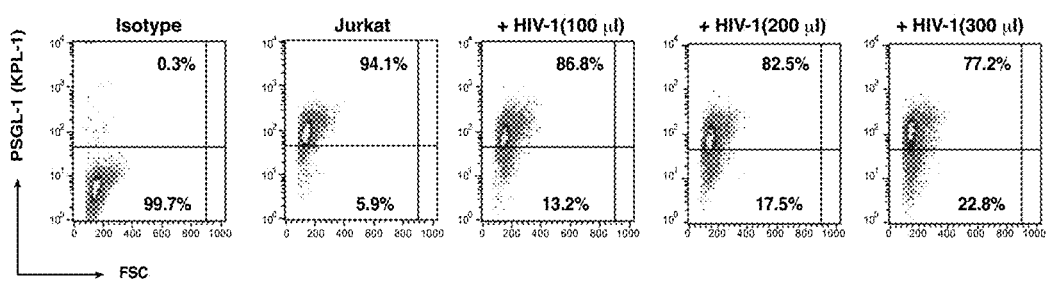
FIG. 12 shows HIV-1 dose-dependent downregulation of PSGL-1 in Jurkat T cells.

FIG. 12 illustrates the HIV-1 dose-dependent downregulation of PSGL-1 in Jurkat T cells. Jurkat T cells were infected with different inputs of HIV-1, washed and cultured for 3 days, and then stained for surface PSGL-1 expression, and analyzed by flow cytometry. Shown are the percentages of cells with high or low PSGL-1 staining in each panel.

Figure 13:
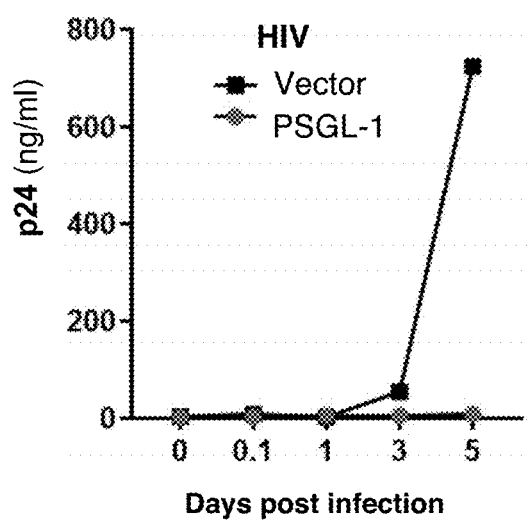
FIG. 13 shows that PSGL-1 blocks the establishment of a spreading HIV-1 infection.

FIG. 13 illustrates that PSGL-1 blocks the establishment of a spreading HIV-1 infection. HEK293T cells (3×106) were cotransfected with 12 μg of HIV(NL4-3) plus 2.4 μg pCMV-PSGL-1 or an empty vector. Viruses were harvested at 48 hours post-transfection and used to infect A3R5.7 CD4 T cells. After infection for 4 hours, cells were washed and cultured for 5 days. HIV replication was analyzed by p24 release.

Figure 14:
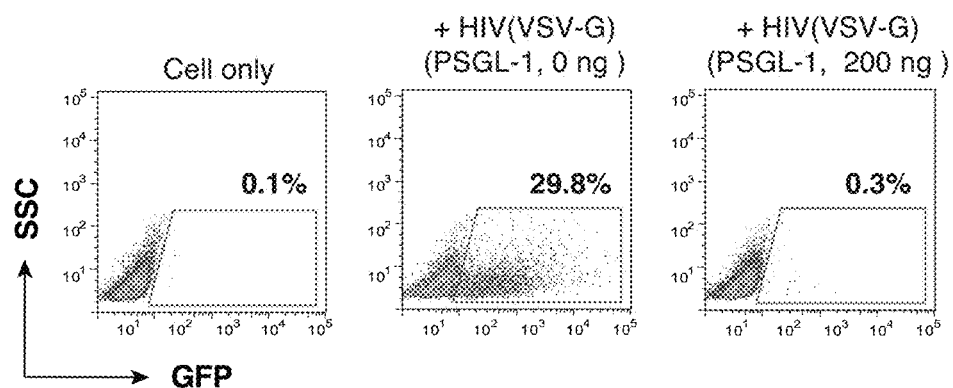
FIG. 14 shows that PSGL-1 inactivates VSV-G pseudotyped HIV-1 virion infectivity.

FIG. 14 illustrates that PSGL-1 inactivates VSV-G pseudotyped HIV-1 virion infectivity. HEK293T cells (2×105) were cotransfected with 1 μg NL4-3 (KFS), 1 μg pHCMV-G, and 200 ng pCMV-PSGL-1 or an empty vector. Virus supernatants were harvested at 48 hours posttransfection, and used to infect Rev-A3R5-GFP cells. After infection for 4 hours, cells were washed and cultured in medium for 72 hours. The percentages of infected (GFP+) cells were quantified by flow cytometry.

Figure 15:
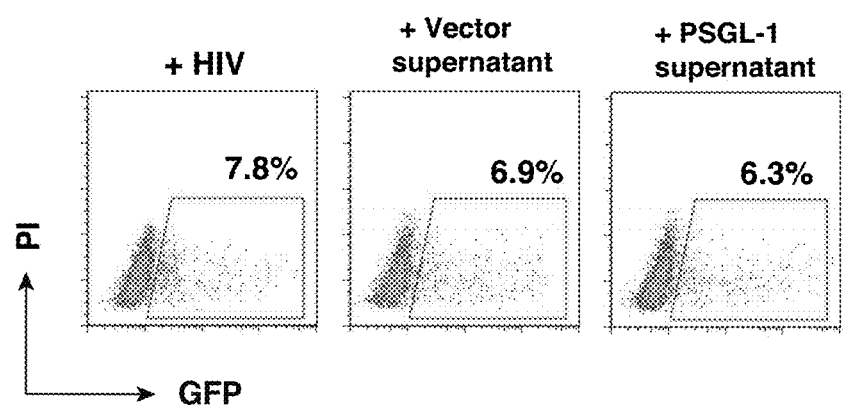
FIG. 15 shows that cell-free PSGL-1 does not inhibit HIV-1 infectivity.

FIG. 15 illustrates that Cell-free PSGL-1 does not inhibit HIV-1 infectivity. HEK293T cells (2×105) were cotransfected with 200 ng of pCMV-PSGL-1 or empty vector. Supernatants were collected at 48 hours posttransfection and mixed with HIV(NL4-3) virus. The mixture was used to infect Rev-A3R5-GFP for 4 hours. Following infection, cells were washed and cultured for 72 hours. The percentages of infected (GFP+) cells were quantified by flow cytometry.

Figure 16:
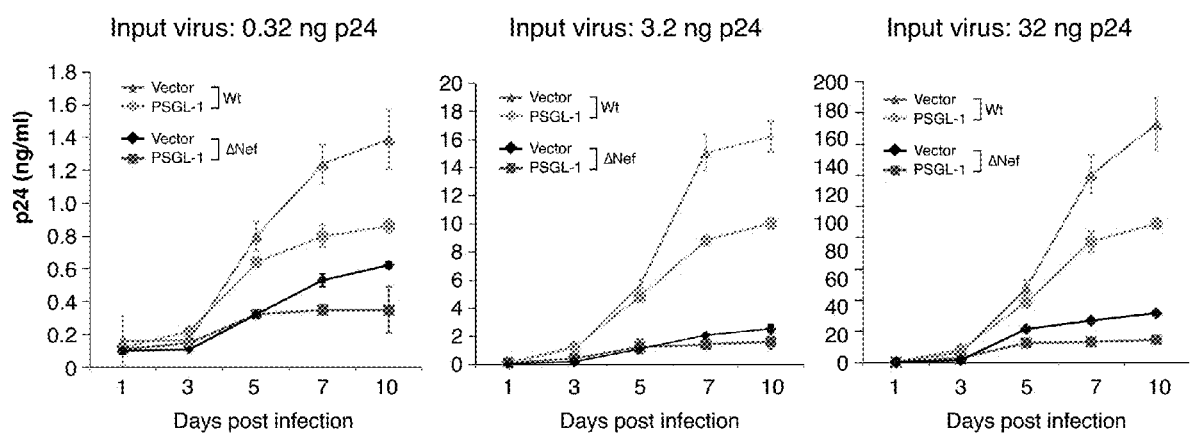
FIG. 16 shows a comparison of PSGL-1 inhibition of HIV-1(WT) and HIV-1(ΔNef) viral replication.
Figure 17A:
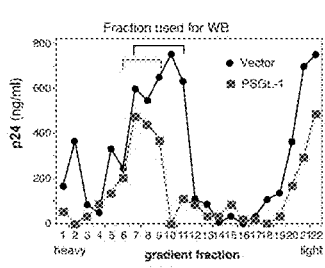
FIGS. 17a-17d show virion incorporation of PSGL-1.
Figure 17B:
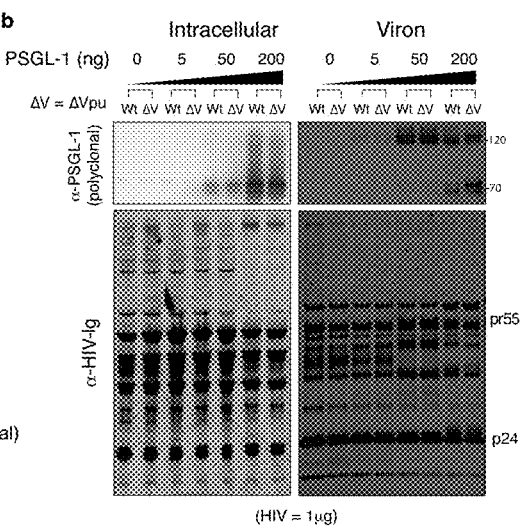
Figure 17C:
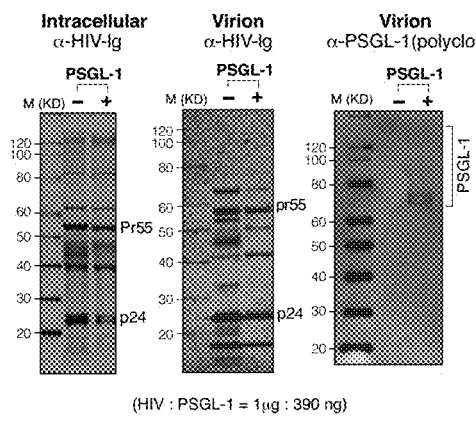
Figure 17D:
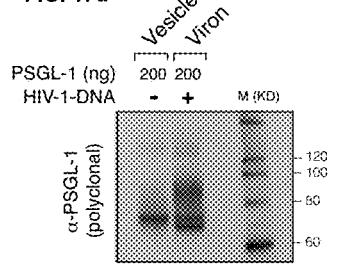

FIG. 16 illustrates the Comparison of PSGL-1 inhibition of HIV-1(WT) and HIV-1(ΔNef) viral replication. HeLa JC.53 cells were stably transfected with PSGL-1 or empty vector DNA, and drug-selected to obtain stably transfected cells. Cells were then infected with 3 different inputs of HIV-1(NL4-3)WT or HIV-1(ΔNef). Viral replication was quantified by p24 release.

FIGS. 17a-17d illustrate the Virion incorporation of PSGL-1. (FIG. 17a to FIG. 17c) HEK293T cells were cotransfected with varying amounts of PSGL-1 DNA plus 1 μg HIV-1(NL4-3) or HIV(ΔVpu) DNA at the indicated ratios. Virion particles were harvested at 48 hours and purified by two rounds of ultra-speed centrifugation through an OptiPrep gradient. Virion proteins were analyzed by western blot using antibodies against PSGL-1 (polyclonal) or HIV-1 proteins (anti-HIV serum). Positions of Gag precursor protein (pr55) and p24 (CA) are indicated. (FIG. 17d) For controls, HEK293T cells were transfected with PSGL-1 DNA only (200 ng) or co-transfected with HIV-1 DNA (1 μg) plus PSGL-1 DNA (200 ng). Extracellular vesicles or virion particles were similarly pelleted by ultracentrifugation, and then analyzed by western blot for the presence of PSGL-1 using the polyclonal antibody.

Example 1

To determine possible effects of PSGL-1 expression on HIV infection, HEK293T cells were cotransfected with HIV(NL4-3) DNA (1000 ng) plus a PSGL-1 expressing vector, using a range of vector dosages from 0.5 to 800 ng. At low dosages (0.5 to 50 ng), PSGL-1 greatly promoted virion release (200 to 400% based on p24). At higher dosages (50 ng and above), the enhancement of virion release was decreased. The empty vector DNA was added during transfection to maintain the same amount of DNA used for cotransfection. However, when intracellular viral proteins were examined, PSGL-1 was found to inhibit intracellular p24 accumulation at dosages higher than 50 ng, and 800 ng PSGL-1 was toxic to cells. Cotransfected cells and extracellular virion particles were lyszed and analyzed by SDS-PAGE and western blot using an anti-PSGL-1 antibody and an anti-HIV antibody. When normalized to intracellular p24, PSGL-1 enhanced virion release at all non-toxic dosages tested. The relative ratio of p24 on the western blot was quantified (extracellular p24/intracellular p24). These results appear to be consistent with an earlier report that PSGL-1 is involved in HIV assembly and budding. It is possible that increasing the amount of PSGL-1 to the sites of HIV assembly promotes virion release.

Example 2

The infectivity of the released virion to infect target CD4 T cells was examined using an HIV Rev-dependent GFP reporter cell line, A3R5-GFP-RRE. Unlike LTR-driving reporter cells, the Rev-dependent report cell strictly requires HIV Rev to turn on GFP expression, which is not affected by cellular factors present in the supernatant of transfected HEK293T cells. Surprisingly, while PSGL-1 promotes virion release, the particles released completely lost infectivity at PSGL-1 vector dosages of 50 ng and higher (HIV: PSGL-1 vector ratio, 1:0.05). HIV particles are also partially inactivated by PSGL-1 at dosages as low as 1-5 ng, and there is a dosage-dependent inactivation of HIV by PSGL-1 at dosages between 1 to 50 ng. HEK293T cells were cotransfected with HIV(NL4-3)DNA (1 ug) plus 400 ng of PSGL-1 expressing vector (PSGL-1). The empty vector DNA (vector) was added during transfection to maintain the same amount of DNA used for cotransfection. At 48 hours post co-transfection, virion particles were harvested and used to infect an HIV Revdependent reporter cells A3R5-GFP-RRE. GFP expression was quantified at 48 hours post infection. An equal p24 level of p24 was used for infection. Cotransfection and infection were done as before. An equal volume of viruses were used the infection of A3R5-GFP-RRE.

Example 3

To determine whether PSGL-1 is incorporated into HIV virion particles, we cotransfected HIV(NL4-3) DNA with the PSGL-1 vector, and purified the virion particles by 2 rounds of high-speed centrifugation, through a gradient of 6-18% OpiPrep solution. HEK293T cells were cotransfected with HIV(NL4-3)DNA (1 ug) plus 200 ng of a PSGL-1 expressing vector (PSGL-1). The empty vector DNA (vector) was added during transfection to maintain the same amount of DNA used for cotransfection. Virions were harvested at 48 hours post cotranfection and purified by ultra-speed centrifugation in OptiPrep gradient solution (1.2-18%). Highly purified virion pellets were analyzed by SDS-PAGE Western blot using an anti-PSGL-1 antibody. We detected the presence of PSGL-1 in virion particles when the blot was probed with an anti-PSGL-1 antibody. In addition, we also probed the blot with anti-HIV antibodies, and detected the presence of various virion proteins. However, the relative ratios of virion proteins were altered. The pol p66/p51/p31, and the p6/p7 proteins were diminished. Virion pellets were analyzed by SDS-PAGE and anti-HIV anti-serum. These results suggest that the incorporation of PSGL-1 may affect the intravirion protease cleavage of virion polyproteins, particularly the gag-pol precursors, which may block the maturation of released virion particles.

Example 4

The mechanism of PSGL-1-mediated inactivation of virion infectivity was further studied by following the early steps of HIV infection. Using an HIV entry assay, the BlaM-Vpr assay, it was observed that the virions produced from PSGL-1 vectorcotransfected cells were not able to enter CD4 T cells, suggesting that virion incorporation of PSGL-1 may affect virion attachment or virus-cell fusion. HEK293T cells were cotransfected with HIV(NL4-3)DNA (1 ug) plus 200 ng of a PSGL-1 expressing vector (PSGL-1). The empty vector DNA (vector) was added during transfection to maintain the same amount of DNA used for cotransfection. Virions were harvested at 48 hours post cotranfection and used to perform a BlaM-Vprbased HIV entry assay. AMD3100 was used as a control. A virion attachment assay was also performed, and it was observed that the virions produced from PSGL-1 vector-cotransfected cells were not able to attach to HIV target cells. Virions were also used to perform a virus attachment assay. Viruses were incubated with target CD4+CXCR4+JC.53 cells at 4 degree for 2 hours. Cells were extensively washed, lyzed, and analyzed by SDS-PAGE and western blot using an anti-HIV p24 antibody. The input viruses used for the attachment assay were also analyzed.

Example 5

We investigated whether PSGL-1-mediated inhibition of viral entry is specific to the HIV envelope-mediated plasma membrane fusion. HIV was pseudo-typed with the VSV-G envelope (vesicular stomatitis virus glycoprotein), which mediates viral entry through endocytosis rather than member fusion. The inhibition of VSV-G pseudo-typed HIV infection was observed, demonstrating that PSGL-1 can block viral entry through both plasma member fusion and endocytosis. PSGL-1 is expected to block the infectivity of multiple viruses. HEK293T cells were cotransfected with HIV(KFS)+pCMV-VSV-G DNA plus a PSGL-1 expressing vector (PSGL-1) or the empty vector DNA (Empty). At 48 hours post co-transfection, virion particles were harvested and used to infect an HIV Rev-dependent reporter cells A3R5-GFP-RRE. GFP expression was quantified at 48 hours post infection.

Example 6

HEK293T cells were cotransfected with HIV(NL4-3) DNA (1 ug) plus 200 ng of a PSGL-1 expressing vector (PSGL-1) or the empty vector (Vector). At 48 hours post cotransfection, virion particles were harvested and used to infect A3R5.7 CD4 T cells or A3R5-GFP-RRE. An equal p24 level of p24 was used for infection. Viral replication was monitored by p24 release. PSGL-1 tranfection supernatant did not inhibit HIV infection. HEK293T cells were transfected with 200 ng of a PSGL-1 expressing vector (PSGL-1) or the empty vector (Vector). Supernatants were harvested at 48 hours, and 400 ul of the supernatants were mixed with 200 ul of HIV-1(NL4-3) virion particles, and then used to infect A3R5-GFP-RRE. For control, 400 ul fresh medium was mixed with HIV. The complete inactivation of HIV infectivity was confirmed by quantifying HIV spreading infection in A3R5 CD4 T cells by p24 release This inactivation of HIV infectivity was not caused by possible cellular factors present in the cotransfection supernatant; the supernatant from PSGL-1 vector-only transfected cells did not inhibit HIV infectivity when mixed with HIV virion particles. Given that PSGL-1 is a membrane protein and is recruited to the sites of virion assembly, it is possible that PSGL-1 may inactivate virion infectivity through direct incorporation into virion particles.

Example 7

To study the potential effects of PSGL-1 expression on HIV-1 replication, we quantified PSGL-1 expression following HIV-1 infection of primary resting CD4 T cells and the transformed Jurkat T-cell line. We observed that human blood resting CD4 T cells express high levels of PSGL-1, and T-cell activation (IL-2 plus PHA) down-regulates PSGL-1, while transformed CD4 T-cell lines express low (e.g. Jurkat) to undetectable (e.g. CEM-SS) levels of PSGL-1. We found that HIV-1 infection of IL-7-treated blood resting CD4 T cells down-regulates PSGL-1 exclusively in the HIV-1+ cell population; culturing resting CD4 T cells in IL-7 permits low-level HIV replication. HIV-1-mediated downregulation of PSGL-1 occurred both in the memory and naïve T-cell populations. We also observed an HIV-1 dose-dependent downregulation of PSGL-1 in infected Jurkat T cells. Thus, HIV-1 actively down-regulates surface PSGL-1 on both primary resting memory and naive CD4 T cells, as well as on transformed T-cell lines.

Example 8

Given the observed PSGL-1 down-regulation by HIV-1, we investigated the role of PSGL-1 in HIV-1 infection and spread. We transiently transfected HeLa JC.53 cells with a PSGL-1 vector (5-50 ng), and then infected the cells with HIV(NL4-3) or an HIV-1 envelope (Env)-pseudotyped, single-cycle virus, HIV(gp160). We observed a dose-dependent inhibition of HIV(NL4-3) in a multi-round, spreading infection, but not in a single-cycle infection. Thus, at these low doses (5-50 ng), PSGL-1 did not block any steps in the viral replication cycle up to the release of virion particles but rather blocked the establishment of a spreading infection.

Example 9

To investigate the effects of PSGL-1 on late steps of the virus replication cycle, we co-transfected HEK293T cells with HIV(NL4-3) DNA (1 μg) plus PSGL-1 expression vector at varying inputs from 0.5 to 800 ng. We observed small effects of PSGL-1 expression on HIV-1 virion release, from slight enhancement at low doses (below 100 ng) to slight inhibition at high doses (800 ng). However, when normalized to the levels of intracellular Gag, PSGL-1 did not inhibit virion release at any dose tested. Next, we quantified the infectivity of the released virions on target CD4 T cells, using a highly stringent Rev-dependent indicator cell line, Rev-A3R5-GFP, that does not respond to non-infectious HIV stimuli as do LTR-based reporter cell lines. We found that while PSGL-1 did not inhibit virion release, it abolished the infectivity of released virions at PSGL-1 vector doses higher than 50 ng. PSGL-1 partially restricted HIV-1 infectivity at inputs as low as 0.5 ng (PSGL-1 DNA to HIV DNA ratio, 1:2000), and there was a dose-dependent inactivation of HIV-1 at PSGL-1 vector doses from 0.5 to 50 ng. The complete inactivation of HIV-1 infectivity was confirmed by quantifying HIV-1 spreading infection in A3R5.7 CD4 T cells by p24 release. In addition, PSGL-1 expression in the virus-producer cell also blocked the infectivity of VSV-G pseudotyped HIV-1. This inactivation of virus infectivity was not caused by soluble PSGL-1 or PSGL-1-containing vesicles present in the cotransfection supernatant, as the supernatant from cells transfected with only PSGL-1 did not inhibit HIV-1 infectivity when mixed with virion particles produced from PSGL-1-negative HEK293T cells. Together, these results demonstrate that the presence of PSGL-1 in producer cells inactivates the infectivity of released virions.

Example 10

We demonstrated that HIV-1 antagonizes PSGL-1 by actively down-regulating it from the T-cell surface. To identify the viral factors responsible for HIV-1-mediated PSGL-1 downregulation, we cotransfected PSGL-1 DNA with Vpu or Nef expression vectors. Both Vpu and Nef are known broad-spectrum modulators of cell-surface receptors. We observed a dose-dependent downmodulation of PSGL-1 levels at the cell surface by both Vpu and Nef, consistent with previous reports. However, when the levels of intracellular PSGL-1 were examined, Vpu but not Nef was found to cause a decrease in total intracellular PSGL-1. Interestingly, Nef induced an intracellular accumulation of the 70-80 kDa species of PSGL-1, suggesting that this low-mobility PSGL-1 may be the form redirected by Nef to intracellular vesicles without being degraded. To confirm the biological role of Vpu and Nef in antagonizing PSGL-1, we cotransfected varying amounts of PSGL-1 DNA with wild-type HIV-1(NL4-3) DNA (WT) or mutants lacking Vpu (HIV-1ΔVpu) or Nef (HIVΔNef) expression. Virions were harvested and their infectivity was quantified on T-cell line-derived Rev-A3R5-GFP indicator cells. For WT HIV-1, we observed a PSGL-1 dose-dependent inhibition of HIV-1 infectivity, with 50% inhibitory dose (IC50) of around 2.71 ng of PSGL-1. For HIV-1ΔVpu, we observed a similar dose-dependent inhibition, but there was a 10-fold difference in the sensitivity to PSGL-1 restriction. The IC50 of PSGL-1 for HIVΔVpu is 0.29 ng. Thus, deletion of Vpu led to a heightened sensitivity to PSGL-1 restriction. There was only a slight difference in IC50s between HIVΔNef and HIV WT. Thus, although both Vpu and Nef can down-regulate PSGL-1 expression from the cell surface, Vpu appears to play the major role in antagonizing PSGL-1 in HEK293T cells. These results were corroborated in spreading infection of PSGL-1-stably transfected HeLa JC.53 cells (HeLaJC53-PSGL-1). WT HIV-1 and HIVΔVpu or HIVΔNef derivatives were produced in HEK293T cells in the absence of PSGL-1, and then used to infect HeLaJC53-PSGL-1 or control HeLaJC53-Empty vector-transfected cells, using p24-normalized inocula. At all 3 HIV-1 inputs, PSGL-1 displayed a stronger inhibition of HIVΔVpu than of WT. At the highest HIV-1 input used (32 ng p24), no spreading viral replication was detected from HIVΔVpu in HeLaJC53-PSGL-1 cells, whereas WT viral replication was only modestly inhibited. In comparison with HIVΔVpu, HIVΔNef was inhibited to a similar degree as the HIV(WT) by PSGL-1. Based on these results, we conclude that although both Vpu and Nef can downregulate PSGL-1 from the surface, Vpu plays the major role in antagonizing PSGL-1. Nevertheless, it is likely that both viral factors work together in a cooperative manner to antagonize PSGL-1.

Example 11

PSGL-1 has been found to co-localize with Gag at sites of HIV-1 Gag assembly in uropod microdomains following Gag multimerization. However, the biological role of PSGL-1/Gag colocalization during HIV virion assembly remains unclear. Given the reported colocalization of Gag and PSGL-1 in virus-producing cells, we asked whether PSGL-1 is incorporated into HIV-1 particles. We co-transfected HIV (NL4-3) DNA with the PSGL-1 expression vector, purified the virion particles by two rounds of ultracentrifugation through an OptiPrep gradient, and analyzed the virion content by western blot. We detected the presence of PSGL-1 in virions. Strikingly, levels of the viral Env glycoprotein subunits gp120 and gp41 were significantly diminished when PSGL-1 was expressed in the producer cell. We also observed a defect in Env precursor gp160 processing to gp120 and gp41 in PSGL-1-expressing cells. Consistent with the reduction in virion-associated Env proteins, we observed diminished virus entry when the PSGL-1-imprinted HIV-1 particles were used to perform a virus entry assay. We further performed a virion attachment assay, and observed that virions from PSGL-1-expressing cells were impaired in their ability to attach to susceptible target cells.
Methods
Examples 7 through 11 relied on the use of the processes and materials described below.

Cells and Viruses

Peripheral blood buffy coats from HIV-1-negative adults were purchased from the New York Blood Center or received from the NIH Blood Bank. CD4+ T cells were isolated by negative selection using the Dynabeads Untouched magnetic separation kit (Invitrogen) or as previously described. CD4+ T cells were cultured in RPMI 1640 plus 10% fetal bovine serum (FBS) and 1× penicillin-streptomycin (Invitrogen). Resting CD4 T cells were activated by culturing in PHA (2 µg/ml) plus IL-2 (2 ng/mL) (PepTech). HEK293T cells (ATCC) and HeLaJC.53 cells (NIH AIDS Reagent Program) were maintained in Dulbecco-modified Eagle's medium (DMEM) (Invitrogen) containing 10% FBS and 1× penicillin-streptomycin (Invitrogen). PSGL-1-HeLaJC53 and Empty-HeLaJC53 cells were cultured in DMEM supplemented with 10% FBS and 550 µg/ml hygromycin B (Invitrogen). TZM-bl cells (NIH AIDS Reagent Program) were cultured in DMEM containing 10% FBS and 1× penicillin-streptomycin (Invitrogen). Jurkat cells (NIH AIDS Reagent Program) were cultured in RPMI 1640 supplemented with 2 mM L-glutamine, 10% FBS and 1× penicillin-streptomycin (Invitrogen). HIV Rev-dependent GFP indicator cells Rev-A3R5-GFP (Virongy) were cultured in RPMI 1640 plus 10% FBS supplemented with 1 µg/ml G418 (Sigma-Aldrich) and 1 µg/ml puromycin (Sigma-Aldrich). A3R5.7 cells (NIH AIDS Reagent Program) were cultured in RPMI-1640 containing 10% FBS, 1% L-Glutamine, 1× penicillin-streptomycin, and 1 µg/mL G418 (Invitrogen). CEM-SS cells (NIH AIDS Reagent Program) were cultured in RPMI-1640 with 10% FBS. To construct PSGL-1-HeLaJC53 cells, HeLaJC.53 cells were seeded into a 6-well plate and cultured in DMEM with 10% FBS. Cells were transfected with 2 µg pCMV3-PSGL-1 or pCMV3-Empty DNA using Jetprime transfection reagent (Polyplus) as recommended by the manufacturer. Transfected cells were cultured and selected with DMEM containing 10% FBS and 550 µg/ml of hygromycin B (Invitrogen) to generate stably transfected cells.

Plasmids, Vectors, and Transfections

The infectious HIV-1 molecular clone pNL4-3, codon-optimized Vpu expression vector (pcDNA-Vphu), Nef expression vector (pNef-ER), and NL4-3 ΔVpu infectious molecular clone (pNL-U35) were obtained from the NIH AIDS Reagent Program. pCMV3-PSGL-1 and pCMV3-Empty vectors were obtained from Sinobiological. pNLA-WEnv (gp160) and pHCMV-G expressing the HIV-1 Env and the vesicular stomatitis virus G glycoprotein, respectively, were described previously. pNL4-3ΔNef was described previously. The env-defective pNL4-3 derivative pNL4-3/KFS was described previously.

The procedure for transfection of HEK293T cells to produce HIV-1 particles was described previously. For transient transfection of HeLaJC.53 cells, 0.5 million cells were transfected with 2 µg of either pCMV3-Empty or pCMV-PSGL-1 using the transfection reagent Jetprime (Polyplus) as recommended by the manufacturer. Following transfection, cells were cultured for the indicated times until analysis. For the p24 release assay in HEK293T cells, cells were cotransfected with 1 µg of HIV-1 NL4-3 and indicated doses of pCMV3-PSGL-1 or pCMV3-Empty DNA using Lipofectamine 2000 (Invitrogen). Supernatant was collected at 48 hours posttransfection. To purify virions by ultracentrifugation, supernatants harvested from transfected HEK293T cells were purified by ultra-speed centrifugation through a gradient of 6-18% OptiPrep solution (Sigma-Aldrich), followed by a second round of ultracentrifugation using a swinging-bucket rotor SW41Ti (Beckman) to pellet the virus (41,000 rpm).

FACS Analysis

For PSGL-1 surface staining, 0.5-1 million cells were stained with anti-PSGL1 antibody [KPL-1] (BD Pharmingen) followed by staining with Alexa Fluor 488-conjugated goat anti-mouse secondary antibody (Invitrogen). For surface staining of infected blood resting CD4+ T cells, HIV-1 infection was done using 125 ng to 320 ng p24 gag equivalents of NLHG1-ES-IRES-GPF reporter virus per million cells. Cells were washed and cultured in 10% FBS RPMI with IL-7 (2 ng/mL). On the indicated days, cells were harvested and stained at 4° C. for 30 min with AF687 anti-PSGL-1 antibody (KPL-1, BD Pharmingen) and analyzed by flow cytometry. For surface PSGL-1 staining of Jurkat, CEM-SS, and A3R5.7 cells, 0.5 million cells were stained with FITC-conjugated anti-PSGL-1 antibody (Abcam) and analyzed by flow cytometry. For HIV-1-infected Jurkat T-cell surface staining, 0.5 million cells were infected with different volumes of HIV-1 NL4-3. At 3 days post infection, cells were stained with anti-PSGL-1 antibody [KPL-1] (BD Pharmingen), followed by staining with Alexa Fluor 488-conjugated goat anti-mouse secondary antibody (Invitrogen) and flow cytometry analysis. For HEK293T cells, 0.5 million cells were cotransfected with different dosages (1 µg to 4 µg) of HIV NL4-3 Vpu or HIV NL4-3 Nef, and 100 ng of pCMV3-PSGL-1 using Lipofectamine 2000 (Invitrogen). Cells were stained at 48 hours posttransfection with anti-PSGL-1 antibody [KPL-1] (BD Pharmingen), followed by staining with Alexa Fluor 488-conjugated goat anti-mouse secondary antibody (Invitrogen).

Western Blots to Detect PSGL-1 and HIV-1 Proteins

The following antibodies were from the NIH AIDS Reagent Program: anti-HIV-1 p24 monoclonal antibody (183-H12-5C), anti-HIV Env (16H3) antibody, anti-HIV-1 gp41 monoclonal antibody (2F5), anti-HIV-1 gp41 monoclonal antibody (10E8), and anti-HIV immune globulin (HIVIG). Cells or virus pellets were solubilized in lysis buffer containing 50 mM Tris-HCl (pH 7.4), 150 mM NaCl, 1 mM EDTA, 0.5% Triton X-100, and protease inhibitor cocktail (Roche Life Science, Basel, Switzerland) or LDS lysis buffer (Invitrogen). Proteins were denatured by boiling in sample buffer and subjected to SDS-PAGE, transferred to PVDF or nitrocellulose membrane, and incubated overnight at 4° C. with one of the following primary antibodies: anti-PSGL-1 (clone KPL-1, BD Pharmingen) (1:1000 dilution); anti-PSGL-1 TC-2 (Abcam) (1:1000 dilution); anti-PSGL-1 polyclonal (Abcam) (1:1000 dilution); anti-GAPDH goat polyclonal antibody (Abcam) (1:1000 dilution); anti-CD45RA antibody (BD Biosciences); or HIVIG; 183-H12-5C, 16H3, 2F5, 10E8, HIVIG. Membranes were then incubated with HRP-labeled goat anti-mouse IgG (KPL) (1:2500 dilution) or anti-rabbit IgG (Cell Signaling) (1:2000 dilution) for 60 min at RT. Chemiluminescence signal was detected by using West Pico or West Femto chemiluminescence reagent (Thermo Fisher Scientific). Images were captured with a CCD camera (FluorChem 9900 Imaging Systems) (Alpha Innotech). Protein bands were also quantified using Imagelab-Chemidoc (Bio-Rad Laboratories, France). On some occasions, western blot was also performed using infrared imaging (Odyssey infrared imager, LI-cor Biosciences) with IRDye goat anti-mouse or rabbit 680 or 800 cw labeled antibodies (Li-cor Biosciences) (1:5000 diluted in blocking buffer) for 1 h at 4° C. The blots were washed three times for 15 minutes and scanned with Odyssey Infrared Imager (Li-cor Biosciences).

The ratios of gp120/p24 and gp160/p24 were quantified in virions, and the ratio of gp120/gp160 and expression of PSGL-1 were quantified in cell and virus fractions. To quantify virus release efficiency, HEK293T cells were transfected with the indicated plasmids (WT pNL4-3, pNL43ΔVpu, or pNL43ΔNef) in the absence or presence of PSGL-1 expression vector using Lipofectamine 2000 (Invitrogen) or polyethylenimine (PEI) transfection reagent (Sigma-Aldrich). At 30 to 48 hours after the addition of DNA, virus-containing supernatant was harvested for p24 ELISA, or filtered and pelleted in an ultracentrifuge for analysis. The viral release efficiency (VRE) was calculated as the amount of virion-associated Gag as a fraction of total (cell- and virion-associated) Gag quantified from Western blot analysis.

p24 ELISA

HIV-1 p24 released into the cell culture supernatant was detected by an in-house p24 ELISA kit. Briefly, microtiter plates (Sigma-Aldrich) were coated with anti-HIV-1 p24 monoclonal antibody (183-H12-5C) (NIH AIDS Reagent Program). Samples were incubated for 2 hours at 37° C., followed by washing and incubating with biotinylated anti-HIV immune globulin (HIVIG) (NIH AIDS Reagent Program) for 1 hour at 37° C. Plates were then washed and incubated with avidin-peroxidase conjugate (Thermo Fisher Scientific) for 1 hour at 37° C., followed by washing and incubating with tetramethylbenzidine (TMB) substrate. Plates were kinetically read using an ELx808 automatic microplate reader (Bio-Tek Instruments) at 630 nm.

Viral Entry Assay (BLAM Assay)

The viral entry assay was performed as previously described. Briefly, viruses were generated by co-transfection of HEK293T cells with three plasmids: pNL4-3, pAdvantage (Promega) and pCMV4-3BlaM-Vpr (kindly provided by Dr. Warner C. Greene) (in a ratio of 6:1:2). Supernatant was harvested at 48 hours posttransfection, concentrated, and then used for infection as suggested. Flow cytometry was performed using a Becton Dickinson LSR II (Becton Dickinson). β-lactamase and CCF2 measurements were performed using a 407-nm violet laser with emission filters of 525/50 nm (green fluorescence) and 440/40 nm (blue fluorescence), respectively. Green and blue emission spectra were separated using a 505LP dichroic mirror. The UV laser was turned off during the analysis. Data analysis was performed using FlowJo software (FlowJo).

Viral Attachment Assay

Virion particles produced in the presence of PSGL-1 or the empty vector were incubated with HelaJC53 cells at 4° C. for 2 hours. The cells were then washed extensively (5 times) with cold PBS buffer and then lysed with LDS lysis buffer (Invitrogen) for analysis by Western blot.

Infectivity Assays

For flow cytometry-based infectivity assay, virus particles were produced in HEK293T cells by cotransfection with pNL43, pNL43ΔVpu, or pNL43ΔNef with pCMV3-PSGL1 or pCMV3-Empty, or by cotransfection with pNL4-3/KFS, pHCMV-G, and pCMV3-PSGL-1 or pCMV3-Empty vector (using the indicated plasmid inputs) in a 6-well plate with Lipofectamine 2000 (Invitrogen). Rev-A3R5-GFP cells were infected with each of the indicated viruses (0.5 million cells/infection). The cells were then washed and cultured in fresh media. Flow cytometry analysis of GFP expression was performed on the indicated days. The percentage of GFP+ cells was quantified.

For luciferase-based, single-cycle infectivity assays, RT-normalized virus stocks were used to infect the CD4+/CXCR4+/CCR5+ HeLa derivative TZM-bl. This indicator cell line contains integrated copies of the β-galactosidase and luciferase genes under the control of the HIV-1 LTR. Infection efficiency was determined by measuring luciferase activity 2 days postinfection. For infectivity assays in HeLa JC53-PSGL-1 and HeLa-JC53-empty cell lines, the cells were seeded in 6-well plates at a density of 0.2×106/well 24 hours prior to infection. Cells were infected with the indicated p24 equivalents of either WT NL4-3, NL43ΔVpu, or NL43ΔNef. Viral replication was quantified by virion p24 released into the medium by p24 ELISA.

The embodiments describe a new approach to producing vaccines comprising live attenuated, inactivated, or non-infectious virion particles, such as HIV particles.

Other embodiments are also within the scope of the following claims.

What is claimed is:

1. A composition comprising:
   a human immunodeficiency virus (HIV) particle with deleted Vpu, wherein a P-selectin glycoprotein ligand-1 (PSGL-1) or a PSGL-1 mutant is incorporated in the HIV particle; wherein the HIV particle comprises a non-infectious HIV particle, an attenuated HIV particle or an inactivated HIV particle.

2. The composition of claim 1, wherein the HIV particle comprises a non-infectious HIV particle.

3. The composition of claim 1, wherein the HIV particle comprises an attenuated HIV particle.

4. The composition of claim 1, wherein the HIV particle comprises an inactivated HIV particle.

5. The composition of claim 1, the HIV particles are produced in a HIV producing cell, and wherein the PSGL-1 or the PSGL-1 mutant is transfected and expressed in the HIV producing cell.

6. The composition of claim 5, wherein the HIV producing cell comprises a HIV capable of producing an infection.

7. The composition of claim 5, wherein the HIV producing cell comprises a HIV.

8. The composition of claim 5, wherein the PSGL-1 or the PSGL-1 mutant is expressed by a vector expressing the PSGL-1 or the PSGL-1 mutant into the HIV producing cell.

9. The composition of claim 5, wherein the PSGL-1 or the PSGL-1 mutant is configured to inhibit the HIV producing cell from producing a HIV capable of producing an infection.

10. The composition of claim 8, wherein the vector expresses the PSGL-1 or the PSGL-1 mutant in dosages from 0.5 to 800 ng in the HIV producing cell.

11. The composition of claim 1, wherein the PSGL-1 or the PSGL-1 mutant is configured to reduce an amount of a Gag precursor protein in the HIV particles.

12. The composition of claim 11, wherein the Gag precursor protein comprises pr55 and p24.

13. The composition of claim 1, wherein the PSGL-1 or the PSGL-1 mutant is configured to alter a relative ratio of virion proteins comprising pol p66/p51/p31 and/or p6/p7.

14. The composition of claim 1, wherein the HIV particle has impaired ability to attach to target cells.

15. The composition of claim 1, wherein the PSGL-1 or the PSGL-1 mutant is configured to reduce virion associated Env protein.

* * * * *